US007363161B2

(12) United States Patent
Georgi et al.

(10) Patent No.: US 7,363,161 B2
(45) Date of Patent: Apr. 22, 2008

(54) PORE-SCALE GEOMETRIC MODELS FOR INTERPRETATION OF DOWNHOLE FORMATION EVALUATION DATA

(75) Inventors: Daniel T. Georgi, Houston, TX (US); Mikhail Gladkikh, The Woodlands, TX (US); Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/445,023

(22) Filed: Jun. 1, 2006

(65) Prior Publication Data

US 2006/0273788 A1 Dec. 7, 2006

Related U.S. Application Data

(63) Continuation-in-part of application No. 11/147,063, filed on Jun. 3, 2005, now Pat. No. 7,257,490, and a continuation-in-part of application No. 11/146,886, filed on Jun. 3, 2005.

(60) Provisional application No. 60/782,076, filed on Mar. 14, 2006.

(51) Int. Cl.
*G01V 3/18* (2006.01)
(52) U.S. Cl. .................. 702/7; 702/9; 702/11; 324/303
(58) Field of Classification Search .................. 702/7, 702/9, 11, 12, 13; 703/10; 324/303
See application file for complete search history.

(56) References Cited

U.S. PATENT DOCUMENTS

| 3,321,625 | A | 5/1967 | Walh ........................ 250/71.5 |
| 4,271,356 | A | 6/1981 | Groeschel et al. .......... 250/262 |
| 4,953,399 | A | 9/1990 | Fertl et al. ..................... 72/152 |
| 5,303,775 | A | 4/1994 | Michaels et al. ........... 166/264 |
| 5,452,761 | A | 9/1995 | Beard et al. ................ 166/250 |
| 6,008,645 | A | 12/1999 | Bowers et al. .............. 324/303 |
| 6,088,656 | A | 7/2000 | Ramakrishnan et al. ...... 702/13 |
| 6,157,893 | A | 12/2000 | Berger et al. .................. 702/9 |
| 6,557,632 | B2 | 5/2003 | Cernosek .................... 166/264 |
| 2001/0054306 | A1 | 12/2001 | Baklanov et al. .............. 73/38 |
| 2002/0153888 | A1 | 10/2002 | Kruspe et al. .............. 324/303 |
| 2002/0173915 | A1 | 11/2002 | Egermann et al. ............ 702/12 |
| 2003/0057947 | A1 | 3/2003 | Ni et al. ...................... 324/309 |
| 2003/0094946 | A1 | 5/2003 | Galford et al. ............. 324/303 |
| 2003/0178994 | A1 | 9/2003 | Hurlimann et al. ......... 324/303 |

(Continued)

OTHER PUBLICATIONS

Per H. Valvatne et al.; *Predictive Pore-Scale Network Modeling*, SPE 84550, SPE Annual Technical Conference and Exhibition, Oct. 5-8, 2003, pp. 1-12, 20 Figs.

(Continued)

*Primary Examiner*—Donald E McElheny, Jr.
(74) *Attorney, Agent, or Firm*—Madan, Mossman & Sriram, P.C.

(57) ABSTRACT

The grain size of a pore-scale geometric model of a clastic earth formation are adjusted so that the NMR relaxation time distribution output of the model matches a measured NMR distribution. Fluid drainage and imbibing can be simulated. Additional properties of the earth formation are predicted using the pore-scale model. The additional properties may be based on additional measurements of properties of a fluid in the formation.

23 Claims, 15 Drawing Sheets

U.S. PATENT DOCUMENTS

| | | |
|---|---|---|
| 2003/0225521 A1 | 12/2003 | Panga et al. .................... 702/6 |
| 2003/0226663 A1 | 12/2003 | Krueger et al. .......... 166/252.5 |
| 2004/0100264 A1 | 5/2004 | Martin et al. ............... 324/346 |
| 2004/0251904 A1 | 12/2004 | Corver et al. ............... 324/321 |
| 2005/0021234 A1 | 1/2005 | Han ........................... 702/13 |
| 2005/0116709 A1 | 6/2005 | Proett et al. ................ 324/303 |
| 2005/0178189 A1 | 8/2005 | Lenormand et al. ........... 73/38 |
| 2005/0206378 A1 | 9/2005 | Hamdan et al. ........... 324/303 |
| 2005/0229680 A1 | 10/2005 | Kfoury et al .................. 73/38 |
| 2006/0097722 A1 | 5/2006 | Scheven ..................... 324/303 |
| 2006/0136135 A1 | 6/2006 | Little et al. .................... 702/13 |
| 2006/0212224 A1 | 9/2006 | Jogi et al. ....................... 702/9 |

OTHER PUBLICATIONS

Bryant et al.; *Prediction of elastic-wave velocities in sandstones using structural models*, Geophysics, vol. 60, No. 2 (Mar.-Apr. 1995), pp. 437-446, 11 Figs., 1 Table.

Fritz Gassmann; *Elastic Waves Through a Packing of Spheres*, Geophysics, vol. 16, Issue4, Oct. 1951, pp. 673-685, 6 Figs.

Toumeline et al.; *A Numerical Assessment of Modern Barehole NMR Interpretation Techniques*, SPE 90539, SPE Annual Technical Conference and Exhibition, Sep. 26-29, 2004, pp. 1-19, 19 Figs.

M. Gladkikh et al.; *Mechanistic Prediction of Capillary Imbibition Curves*, SPE Annual Technical Conference and Exhibition, Sep. 26-29, 2004, pp. 1-7, 13 Figs.

Lecture notes; CENG 571, Rice University, Spring 2004, pp. 3-1-3-16.

B.F. Swanson; *A Simple Correlation Between Permeabilities and Mercury Capillary Pressures*, Journal of Petroleum Technology, Dec. 1981, pp. 2498-2504.

Steven L. Bryant et al.; *Network Model Evaluation of Permeability and Spatial Correlation in a Real Random Sphere Packing*, Transport in Porous Media 11: 1993, pp. 53-70.

Steven Bryant et al., *Quantification of Spatial Correlation in Porous Media and Its Effect on Mercury Porosimetry*, Journal of Colloid and Interface Science 177, (1996), pp. 88-100, 10 Figs.

Steven Bryant et al.; *Prediction of relative permeability in simple porous media*, Physical Review A, vol. 46, No. 4, Aug. 15, 1992, pp. 2004-2011, 6 Figs.

Martin J. Blunt et al.; *Detailed physics, predictive capabilities and macroscopic consequences for pore-network models of multiphase flow*, Elsevier, Advances in Water Resources 25 (2002), pp. 1069-1089.

PORE-SCALE GEOMETRIC MODELS FOR INTERPRETATION OF DOWNHOLE FORMATION EVALUATION DATA

CROSS-REFERENCES TO RELATED APPLICATIONS

This application claims priority from U.S. Provisional Patent Application Ser. No. 60/782,076 filed on 14 Mar. 2006. This application is also a continuation-in-part of U.S. patent application Ser. No. 11/147,063 filed on 3 Jun. 2005 now U.S. Pat. No. 7,257,490 and U.S. patent application Ser. No. 11/146,886 filed on 3 Jun. 2005.

FIELD OF THE INVENTION

The invention is related generally to methods of interpretation of properties of subterranean earth formations using measurements made by a formation evaluation sensor or sensors. Specifically, the invention is directed towards the use of modeling methods that enable the prediction of properties that are not measured by the formation evaluation sensor or sensors.

BACKGROUND OF THE ART

Oil or gas wells are often surveyed to determine one or more geological, petrophysical, geophysical, and well production properties ("parameters of interest") using electronic measuring instruments conveyed into the borehole by an umbilical such as a cable, a wireline, slickline, drill pipe or coiled tubing. Tools adapted to perform such surveys are commonly referred to as formation evaluation (FE) tools. These tools use electrical, acoustical, nuclear and/or magnetic energy to stimulate the formations and fluids within the borehole and measure the response of the formations and fluids. The measurements made by downhole instruments are transmitted back to the surface.

In order to reduce the amount of rig time needed for wireline logging, it is common practice to run multiple sensors in a single run. FOCUS™, from Baker Atlas Inc., is a high efficiency premium open hole logging system. All of the downhole instruments have been redesigned, incorporating advanced downhole sensor technology, into shorter, lighter, more reliable logging instruments, capable of providing formation evaluation measurements with the same precision and accuracy as the industry's highest quality sensors, at much higher logging speeds. Logging speeds are up to twice the speed of conventional triple-combo and quad combo logging tool strings. Speeds of up to 3600 ft/hr (1080 m/min) are possible. The logging system may include four standard major open-hole measurements (resistivity, density, neutron, acoustic) plus auxiliary services.

Some petrophysical properties are easily obtained from downhole FE measurements. These include porosity, bulk density, NMR relaxation $T_1$ and $T_2$ spectra, and compressional and shear wave velocities. Other petrophysical properties that are of importance in reservoir evaluation and development are difficult if not impossible to measure. Properties that are difficult or impossible to measure include, for example permeability, relative permeability, resistivity formation factor, capillary pressure, and NMR surface relaxivity. These are typically derived from correlations or petrophysical relationships.

One of the problems with relating the different petrophysical properties of an earth formation to each other is that they are all macroscopically measured quantities that depend ultimately on the microscopic arrangement of the constituents of the earth formation. An early attempt at predicting macroscopic properties based on microscopic models is due to Gassmann (1951) in which the earth formation is modeled as a hexagonal close packing of equal-sized elastic spheres. Based on this simplistic model, it is possible to predict the stress dependence of the packing in terms of the moduli of the constituent spheres.

The earth, of course, is not made out of a hexagonal close packing of equal-size elastic spheres. Finney (1968) measured the spatial coordinates of some 8000 spheres in a random packing of spheres, thereby completely determining the geometry of the microstructure of the packing. This packing may be regarded as a physical model of a clean sediment of well-sorted sand grains. The term "sorting" refers to the distribution of grain sizes: a poorly sorted sandstone has a large range of grain sizes while a well sorted sandstone has grains of substantially the same size. Such sediments can be deposited in a wide spectrum of depositional environments, from nonmarine to basinal deep water. The model developed by Finney is primarily applicable to earth formations comprised of compacted clastic sediments. The term "clastic" refers to rocks made up of fragments of preexisting rocks. Based on the model of Finney, there have been numerous papers that discuss the prediction of formation properties. For example, Bryant and Raikes (1995) used the central core of 3367 spheres in Finney's pack, which has a porosity of 36.2% to try to predict elastic wave velocities in sandstones. In Toumelin et al. (2004), the NMR response of porous rocks was simulated using a continuous, three-dimensional (3D) random-walk algorithm. Diffusion pathways of individual fluid molecules are determined within the 3-D porous model. The method of Toumelin allows the rigorous treatment of $T_1$ and $T_2$ relaxation times with a minimum of assumptions and for arbitrary pulse sequences. Toumelin also discusses the numerical accuracy of the simulation. The results reproduce NMR decay and build-up while accounting for restricted diffusion in porous media, fluid wettabilities, and fluid spatial distributions.

By far the greatest amount of work using pore scale models has been in the area of determination of formation permeability. Valvatne et al. (2003) use pore-scale modeling in which the pore-size distribution is altered to match the capillary injection pressure for different tock types. In addition, for water flooding, contact angles are adjusted to match the measured wettability indices. Gladkikh and Bryant (2004) discuss the use of pore-scale modeling of wetting phase imbibition in porous media. Much of the pioneering work in pore-scale modeling for permeability determination is discussed in papers co-scale by Bryant. What is lacking in prior art is a compact discussion of the interrelation between the different petrophysical parameters that may be determined, and their applicability to hydrocarbon exploration in clastic sediments. The present invention addresses this need.

SUMMARY OF THE INVENTION

One embodiment of the invention is a method of evaluating an earth formation containing clastics. NMR signals indicative of a property of the earth formation are obtained. A pore-scale model including grains of the clastics is defined. An NMR response is simulated using the pore-scale model. A parameter of the pore-scale model is adjusted using the simulated response and the NMR signals. The simulated NMR response may include an NMR relaxation time spectrum and adjusting the parameter may be based on deriving a magnetization relaxation spectrum from the NMR signals and using the difference between the NMR relaxation time spectrum and the magnetization relaxation spectrum. The magnetization relaxation spectrum may be derived for a wetting phase that may be oil or water. The parameter being adjusted may be the grain size in the pore-scale model. The simulated NMR relaxation time spectrum may be obtained using a saturation of the wetting phase. Simulations may be made for imbibition or drainage. The difference may be reduced using a least-squares minimization. The pore scale model with the adjusted parameter may be used to simulate an additional property of the earth formation. The additional property may be a permeability, formation factor, and/or a surface to volume probability distribution. The simulation of the spectrum may include adding material to a pore space of the model, accounting for quartz overgrowth, accounting for pore-filling dispersed clay, and/or accounting for compaction. The derived and the simulated spectra may be a $T_1$ spectrum and/or a $T_2$ spectrum. It should be noted that the terms "magnetization relaxation spectrum" and "NMR relaxation time spectrum" refer to the same property of the earth formation and the sole reason for using different terms is that the former is used with reference to a property derived from a measurement while the latter is used with reference to a simulated property.

Another embodiment of the invention is an apparatus for evaluating an earth formation containing sediments. The apparatus includes a Nuclear Magnetic Resonance (NMR) sensor conveyed in a borehole in the earth formation. A processor defines a pore-scale model of the earth formation, the model including grains of clastics, and simulates an NMR response using the defined pore-scale model. The processor adjusts a parameter of the pore-scale model using the simulated NMR response and NMR signals obtained by the sensor. The processor may simulate the NMR response by simulating an NMR relaxation time spectrum. The processor may derive a magnetization relaxation spectrum from the NMR signals and adjust the parameter using a difference between the NMR relaxation time spectrum and the magnetization spectrum. The pore-scale model may include grains and the parameter adjusted by the processor may be a grain size in the model. The processor may simulate the NMR relaxation time spectrum by using a drainage of a wetting fluid in pore-spaces of the model, and/or imbibition of a wetting fluid in pore-spaces of the model. The processor may derive the magnetization relaxation spectrum using a wetting phase of water or oil. The processor may simulate the NMR relaxation time spectrum by further using drainage of a wetting fluid in pore-spaces of the model or imbibition of a wetting fluid in pore-spaces of the model. The processor may adjust the parameter by a least squares minimization. The processor may further use the pore-scale model to simulate an additional property of the earth formation. The additional property may be a permeability, a formation factor, and/or an S/V probability distribution function. The processor may simulate the NMR response by adding a material to a pore space of the model, accounting for quartz overgrowth, accounting for pore-filling dispersed shale, and/ or accounting for compaction. The apparatus may include a conveyance device which conveys the NMR sensor into the borehole. The conveyance device may be a wireline or a drilling tubular.

Another embodiment of the invention is a computer readable medium for use with an apparatus for evaluating an earth formation containing clastic sediments. The apparatus includes a Nuclear Magnetic Resonance NMR) sensor conveyed in a borehole in the earth formation. The medium includes instructions which enable a processor to define a pore-scale model of the earth formation, the pore scale model including grains of the clastic material, simulating an NMR response and adjusting a parameter of the pore-scale model based on the NMR response and measurements made by the NMR sensor. The instructions further enable the processor to estimate from the pore scale model a value of an additional property of the earth formation. The computer readable medium may be a ROM, an EPROM, an EAROM, a Flash Memory, and/or an Optical disk.

BRIEF DESCRIPTION OF THE FIGURES

The present invention is discussed with reference to specific logging instruments that may form part of a string of several logging instruments for conducting wireline logging operations. It is to be understood that the choice of the specific instruments discussed herein is not to be construed as a limitation and that the method of the present invention may also be used with other logging instruments as well. The present invention is best understood with reference to the accompanying figures in which like numerals refer to like elements and in which:

FIG. 4b (prior art) shows the effect of compaction on the arrangement of FIG. 4a;

We begin our discussion of the present invention with an overview of the different types of formation evaluation sensors whose output may be used with the method. This is followed by a discussion of some exemplary prior art methods related to pore-scale modeling of earth formations and their use in predicting macroscopic properties of earth formations that can be measured by formation evaluation sensors. Following this, the method of the present invention is discussed. It should be noted that the term "formation" as used herein includes "formation fluids."

Figure 1:
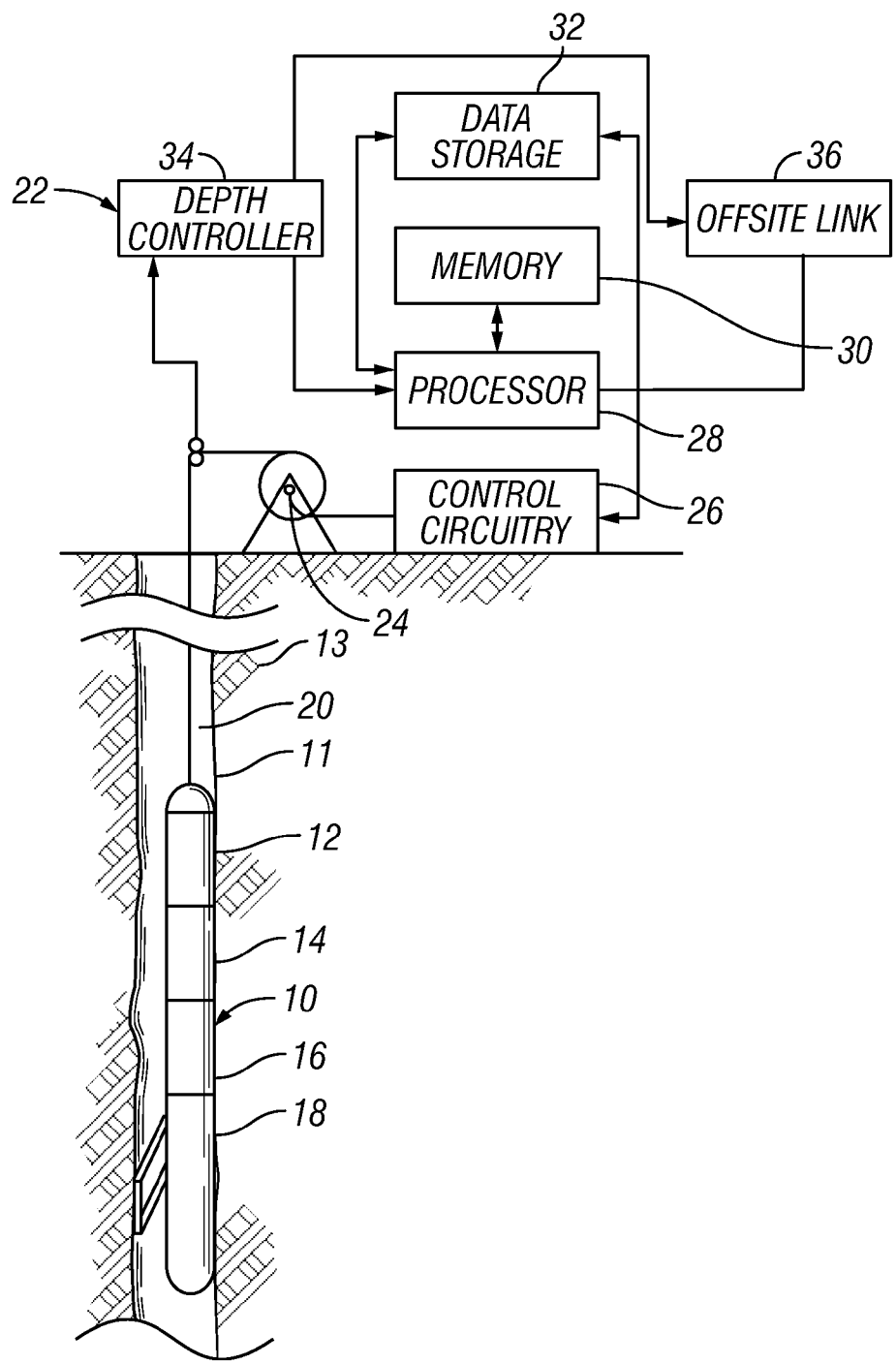
FIG. 1 (prior art) is a schematic illustration of a wireline logging system including a plurality of sensors.

A typical configuration of the logging system is shown in FIG. 1. This is a modification of an arrangement from U.S. Pat. No. 4,953,399 to Fertl et al. having the same assignee as the present invention and the contents of which are incorporated herein by reference. Shown in FIG. 1 is a suite of logging instruments 10, disposed within a borehole 11 penetrating an earth formation 13, illustrated in vertical section, and coupled to equipment at the earth's surface in accordance with the method and apparatus for determining characteristics of clay-bearing formations of the present invention. Logging instrument suite 10 may include a resistivity device 12, a natural gamma ray device 14, and two porosity-determining devices, such as a neutron device 16 and a density device 18. Collectively, these devices and others used in the borehole for logging operations are referred to as formation evaluation sensors. Resistivity device 12 may be one of a number of different types of instruments known to the art for measuring the electrical resistivity of formations surrounding a borehole so long as such device has a relatively deep depth of investigation. For example, a HDIL (High Definition Induction Logging) device such as that described in U.S. Pat. No. 5,452,761 to Beard et al. having the same assignee as the present invention and the contents of which are fully incorporated herein by reference may be used. Natural gamma ray device 14 may be of a type including a scintillation detector including a scintillation crystal cooperatively coupled to a photomultiplier tube such that when the crystal is impinged by gamma rays a succession of electrical pulses is generated, such pulses having a magnitude proportional to the energy of the impinging gamma rays. Neutron device 16 may be one of several types known to the art for using the response characteristics of the formation to neutron radiation to determine formation porosity. Such a device is essentially responsive to the neutron moderating properties of the formation. Density device 18 may be a conventional gamma-gamma density instrument such as that described in U.S. Pat. No. 3,321,625 to Wahl, used to determine the bulk density of the formation. A downhole processor may be provided at a suitable location as part of the instrument suite.

Instrument suite 10 is conveyed within borehole 11 by a cable 20 containing electrical conductors (not illustrated) for communicating electrical signals between instrument suite 10 and the surface electronics, indicated generally at 22, located at the earth's surface. Logging devices 12, 14, 16 and 18 within instrument suite 10 are cooperatively coupled such that electrical signals may be communicated between each device 12, 14, 16 and 18 and surface electronics 22. Cable 20 is attached to a drum 24 at the earth's surface in a manner familiar to the art. Instrument suite 10 is caused to traverse borehole 11 by spooling cable 20 on to or off of drum 24, also in a manner familiar to the art.

Surface electronics 22 may include such electronic circuitry as is necessary to operate devices 12, 14, 16 and 18 within instrument suite 10 and to process the data therefrom. Some of the processing may be done downhole. In particular, the processing needed for making decisions on speeding up (discussed below) for slowing down the logging speed is preferably down downhole. If such processing is done downhole, then telemetry of instructions to speed up or slow down the logging could be carried out substantially in real time. This avoids potential delays that could occur if large quantities of data were to be telemetered uphole for the processing needed to make the decisions to alter the logging speed. It should be noted that with sufficiently fast communication rates, it makes no difference where the decision making is carried out. However, with present data rates available on MWD/LWD, the decision making is preferably done downhole.

Control circuitry 26 contains such power supplies as are required for operation of the chosen embodiments of logging devices within instrument suite 10 and further contains such electronic circuitry as is necessary to process and normalize the signals from such devices 12, 14, 16 and 18 in a conventional manner to yield generally continuous records, or logs, of data pertaining to the formations surrounding borehole 11. These logs may then be electronically stored in data storage 32 prior to further processing. The processor 28 includes the ability, such as that described in U.S. Pat. No. 4,271,356 to Groeschel et al, for separating radiation measurements from natural gamma ray device 14 into individual energy bands centered about energy peaks of selected elemental sources of radiation, preferably the energy peaks of potassium, uranium and thorium. This processing of the natural gamma ray device could also be done by the downhole processor.

Surface electronics 22 may also include such equipment as will facilitate machine implementation of the method of the present invention. Processor 28 may be of various forms but preferably is an appropriate digital computer programmed to process data from logging devices 12, 14, 16 and 18. Memory unit 30 and data storage unit 32 are each of a type to cooperatively interface with processor 28 and/or control circuitry 26. Depth controller 34 determines the longitudinal movement of instrument suite 20 with borehole 11 and communicates a signal representative of such movement to processor 28. The logging speed is altered in accordance with speedup or slowdown signals that may be communicated from the downhole processor, or provided by the surface processor, as discussed below. This is done by altering the rotation speed of the drum 24. Offsite communication may be provided, for example by a satellite link, by the telemetry unit 36.

While running different logging instruments in a single wireline run, the present invention may use a configuration disclosed in U.S. patent application Ser. No. 10/780,167 of Frost et al. filed on Feb. 17, 2004. The teachings of Frost recognize the fact that different logging instruments operate best at different standoffs from the borehole wall.

Figure 2:
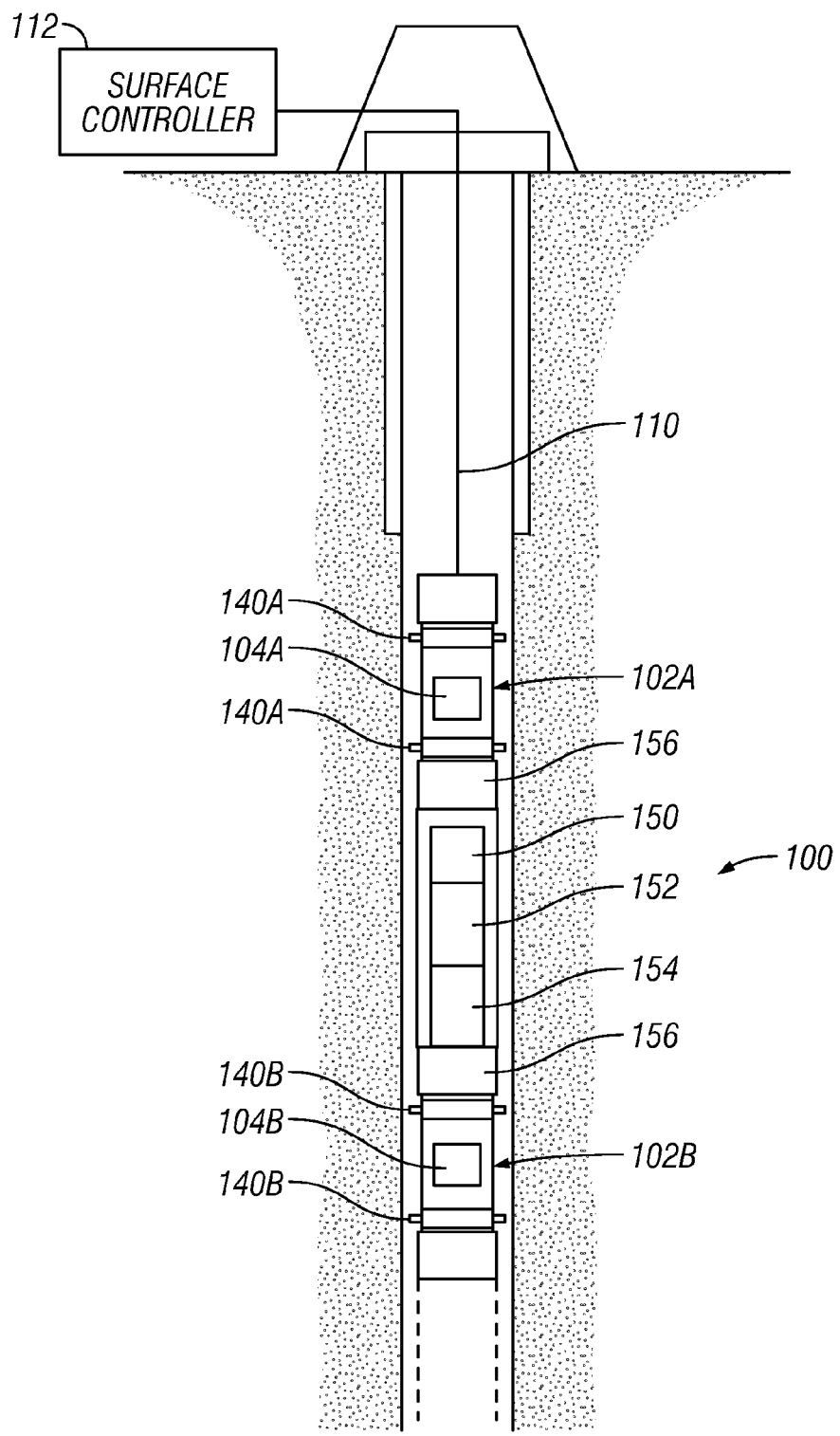
FIG. 2 (prior art) is an elevational view of a system using radially adjustable module adapted for use in logging operations.

Referring next to FIG. 2, there is shown a rig 110 on the surface that is positioned over a subterranean formation of interest. The rig 110 can be a part of a land or offshore a well production/construction facility. A borehole formed below the rig 110 includes a cased portion 142 and an open-hole portion 111. In certain instances (e.g., during drilling, completion, work-over, etc.), a logging operation is conducted to collect information relating to the formation and the borehole. Typically, a tool system 100 is conveyed downhole via a wireline 120 to measure one or more parameters of interest relating to the borehole and/or the formation 113. The term "wireline" as used hereinafter includes a cable, a wireline, as well as a slickline. The tool system 100 can include an instrument suite comprising one or more modules 102a, b, each of which has a tool or a plurality of tools 104a, b, adapted to perform one or more downhole tasks. The term "module" should be understood to be a device such as a sonde or sub that is suited to enclose, house, or otherwise support a device that is to be deployed into a borehole. While two proximally positioned modules 102a, b and two associated tools 104a, b, are shown, it should be understood that a greater or fewer number may be used.

In one embodiment, the tool 104a is a formation evaluation sensor adapted to measure one or more parameters of interest relating to the formation or borehole. It should be understood that the term formation evaluation sensor encompasses measurement devices, sensors, and other like devices that, actively or passively, collect data about the various characteristics of the formation, directional sensors for providing information about the tool orientation and direction of movement, formation testing sensors for providing information about the characteristics of the reservoir fluid and for evaluating the reservoir conditions. The formation evaluation sensors may include resistivity sensors for determining the formation resistivity and dielectric constant, acoustic sensors for determining the acoustic porosity of the formation and the bed boundary in formation, nuclear sensors for determining the formation density, neutron porosity and certain rock characteristics, nuclear magnetic resonance sensors for determining the porosity and other petrophysical characteristics of the formation. The direction and position sensors may include a combination of one or more accelerometers and one or more gyroscopes or magnetometers. The accelerometers preferably provide measurements along three axes. The formation testing sensors collect formation fluid samples and determine the properties of the formation fluid, which include physical properties and chemical properties. Pressure measurements of the formation provide information about the reservoir characteristics and the net confining stress.

The tool system 100 can include telemetry equipment 150, a local or downhole controller (processor)152 and a downhole power supply 154. The telemetry equipment 150 provides two-way communication for exchanging data signals between a surface controller 112 and the tool system 100 as well as for transmitting control signals from the surface processor 112 to the tool system 100.

In an exemplary arrangement, and not by way of limitation, a first module 102a includes a tool 104a configured to measure a first parameter of interest and a second module 102b includes a tool 104b that is configured to measure a second parameter of interest that is either the same as or different from the first parameter of interest. In order to execute their assigned tasks, tools 104a and 104b may need to be in different positions. The positions can be with reference to an object such as a borehole, borehole wall, and/or other proximally positioned tooling. Also, the term "position" is meant to encompass a radial position, inclination, and azimuthal orientation. Merely for convenience, the longitudinal axis of the borehole ("borehole axis") will be used as a reference axis to describe the relative radial positioning of the tools 104a, b. Other objects or points can also be used as a reference frame against which movement or position can be described. Moreover, in certain instances, the tasks of the tools 104a, b can change during a borehole-related operation. Generally speaking, tool 104a can be adapted to execute a selected task based on one or more selected factors. These factors can include, but not limited to, depth, time, changes in formation characteristics, and the changes in tasks of other tools.

Modules 102a and 102b may each be provided with positioning devices 140a, 140b, respectively. The positioning device 140 is configured to maintain a module 102 at a selected radial position relative to a reference position (e.g., borehole axis). The position device 140 also adjusts the radial position of module 102 upon receiving a surface command signal and/or automatically in a closed-loop type manner. This selected radial position is maintained or adjusted independently of the radial position(s) of an adjacent downhole device (e.g., measurement tools, sonde, module, sub, or other like equipment). An articulated member, such a flexible joint 156 which couples the module 102 to the tool system 100 provides a degree of bending or pivoting to accommodate the radial positioning differences between adjacent modules and/or other equipment (for example a processor sonde or other equipment). In other embodiments, one or more of the positioning devices has fixed positioning members.

The positioning device 140 may include a body 142 having a plurality of positioning members 144(a, b, c) circumferentially disposed in a space-apart relation around the body 142. The members 144(a, b, c) are adapted to independently move between an extended position and a retracted position. The extended position can be either a fixed distance or an adjustable distance. Suitable positioning members 144(a,b,c) include ribs, pads, pistons, cams, inflatable bladders or other devices adapted to engage a surface such as a borehole wall or casing interior. In certain embodiments, the positioning members 144(a, b, c) can be configured to temporarily lock or anchor the tool in a fixed position relative to the borehole and/or allow the tool to move along the borehole.

Drive assemblies 146(a, b, c) are used to move the members 144(a, b, c). Exemplary embodiments of drive assemblies 146(a, b, c) include an electromechanical system (e.g., an electric motor coupled to a mechanical linkage), a hydraulically-driven system (e.g., a piston-cylinder arrangement fed with pressurized fluid), or other suitable system for moving the members 144(a, b, c) between the extended and retracted positions. The drive assemblies 146(a, b, c) and the members 144(a, b, c) can be configured to provide a fixed or adjustable amount of force against the borehole wall. For instance, in a positioning mode, actuation of the drive assemblies 146(a, b, c) can position the tool in a selected radial alignment or position. The force applied to the borehole wall, however, is not so great as to prevent the tool from being moved along the borehole. In a locking mode, actuation of the drive assembly 146(a, b, c) can produce a sufficiently high frictional force between the members 144 (a, b, c) and the borehole wall as to prevent substantial relative movement. In certain embodiments, a biasing member (not shown) can be used to maintain the positioning members 144(a, b, c) in a pre-determined reference position. In one exemplary configuration, the biasing member (not shown) maintains the positioning member 144(a, b, c) in the extended position, which would provide centralized positioning for the module. In this configuration, energizing the drive assembly overcomes the biasing force of the biasing member and moves one or more of the positioning members into a specified radial position, which would provide decentralized positioning for the module. In another exemplary configuration, the biasing member can maintain the positioning members in a retracted state within the housing of the positioning device. It will be seen that such an arrangement will reduce the cross sectional profile of the module and, for example, lower the risk that the module gets stuck in a restriction in the borehole.

The positioning device 140 and drive assembly 146(a, b, c) can be energized by a downhole power supply (e.g., a battery or closed-loop hydraulic fluid supply) or a surface power source that transmits an energy stream (e.g., electricity or pressurized fluid) via a suitable conduit, such as the umbilical 120. Further, while one drive assembly (e.g., drive assembly 146a) is shown paired with one positioning member 144 (e.g., position member 144a), other embodiments can use one drive assembly to move two or more positioning members. The outputs of formation evaluation sensors of the type discussed above, and the outputs of other sensors are used in the present invention in conjunction with pore-scale modeling of earth formations.

Figure 3:
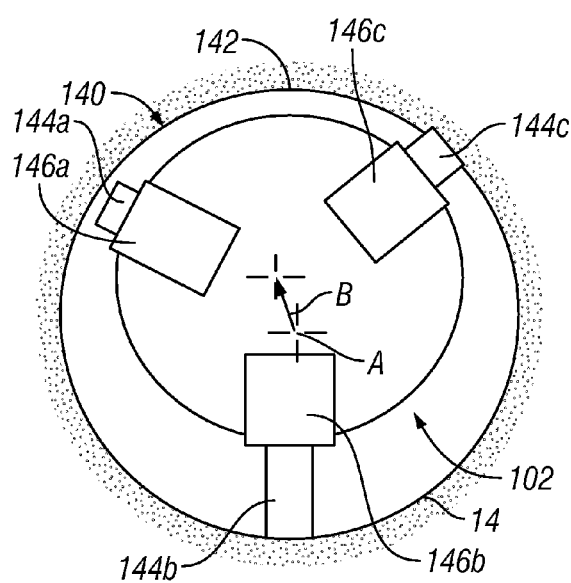
FIG. 3 (prior art) is a cross-sectional view of radially adjustable module positioned in an open hole portion of a borehole.

The method of the present invention is based upon the use of pore-scale modeling together with measurements that may be made by one or more FE sensors including but not limited to the types discussed above with reference to FIGS. 1-3. Before discussing the method of the present invention, we briefly review some of the basic concepts involved in pore-scale modeling.

Sedimentary rocks are traditionally classified using petrographic models. The models are used to distinguish between lithologies differing in mineralogy and matrix materials composed predominately of either terrigenous material or biochemical and inorganic chemical precipitants. The two major lithologies derived from these distinctions are "clastic" versus "carbonate" rocks. The term "carbonate" as used in Ramakrishnan (U.S. Pat. No. 6,088,656) refers to biochemical rocks which are precipitated from water chemistry due to the metabolic processes of organisms. In a broad context, they are commonly referred to as "limestones" however their classification is further refined using other parameters. Carbonate rocks are classified according to their proportion of fine grained carbonate grains (carbonate mud) versus larger grains known as "allochems". Allochems include intraclasts, ooilites, pelloids, and fossil fragments. The most widely used classification is that of Dunham.

In contrast to carbonate classifications, clastic sedimentary rock classifications are based on varying proportions of clasts of different material and grain size composed of minerals and rock fragments. The term "clastic" is derived from a Greek word meaning broken. The accumulation of this terrigenous material is the direct result of the following dynamic subaerial and subaqueous processes: (1) gravity driven mass wasting (downslope slides), (2) winds resulting from atmospheric phenomena such as found in the aeolian environment, (3) gravity driven flowing water (fluvial and alluvial), and (4) tide and wind driven wave energy(nearshore). Subaqueous processes also include (a) gravity driven sedimentation forcing the deposition of suspended sediment onto the floor of water bodies (pelagic and lacustrian sedimentation), (b) thermally forced current flow, and (c) gravity forced turbid flow of water-saturated sediments (turbidity flow). The present invention is directed towards clastic sediments.

Figure 4A:
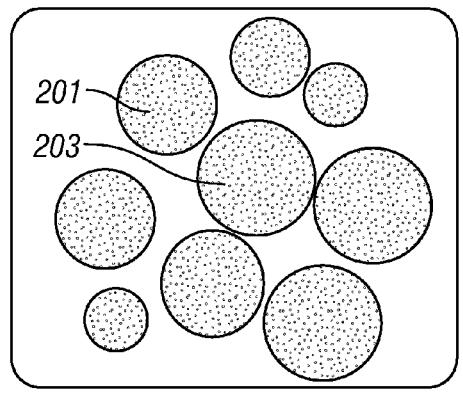
FIG. 4a (prior art) shows a 2-D slice through a random packing of equal spheres.
Figure 4B:
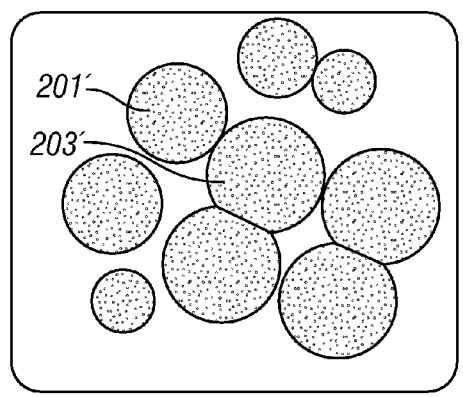
Figure 4C:
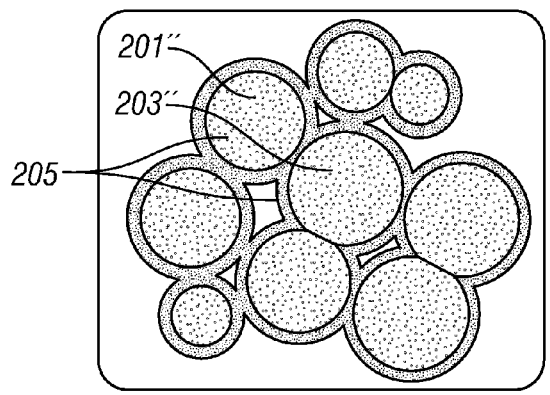
FIG. 4c (prior art) shows quartz overgrowth cementation.

A pore scale model of spheres is the starting point for the characterization of clastic sediments. Shown in FIG. 4a is a 2-D slice through a random packing of equal sized spheres, two of which are denoted as 201, 203. Note that in the 2-D slice, they appear to be of different sizes due to the fact that in the third dimension, they are displaced different distances from the plane of the 2-D slice. Compacting the spheres due to an external stress causes them to interpenetrate as shown by 201', 203'. Note the reduced distance between the spheres. Quartz overgrowth leads to deposition of cement (denoted by 205) and the positions of the two exemplary spheres is now 201", 203". As discussed by Bryant and Raikes, the compaction is equivalent to a rescaling of one of the coordinate axes of Finney:

$$x'_j = x_{j0} + \lambda(x_j - x_{j0}) \qquad (1),$$

where $x_{j0}$ is an arbitrary reference value and $\lambda$ quantifies the degree of compaction. A physically reasonable value of $\lambda$ is $0.7 < \lambda < 1.0$, corresponding to a range of 30% to 0% decrease in bulk volume. For simplicity, Bryant and Raikes assume no deformation of the spheres. The cementation by quartz overgrowth is simulated by increasing the radius of the spheres in the packing without altering the location of the sphere centers:

$$R'_i = R_i + \Delta R_i \qquad (2),$$

where Ri is the radius of the i-th sphere. In one embodiment of the present invention, it is assumed that all grains grow uniformly, i.e., that $\Delta R$ is constant. This is the assumption made in Bryant and Raikes. In an alternate embodiment of the invention, this assumption is not made. It should be noted that other types of overgrowth, such as calcite overgrowth, may also be part of the model. All that is necessary is to change the elastic properties of the overgrowth material.

Bryant and Raikes next discuss the elastic moduli corresponding to the pore-scale model. Specifically, the Biot-Gassmann theory is used. This theory requires four parameters. They are the porosity $\phi$, the tortuosity $\tau$, the bulk modulus $K_b$ and the grain bulk modulus $G_b$. It should be noted that instead of the bulk moduli, other parameters such as the shear moduli and/or Poisson's ratio may also be used in the formulation.

Figure 5:
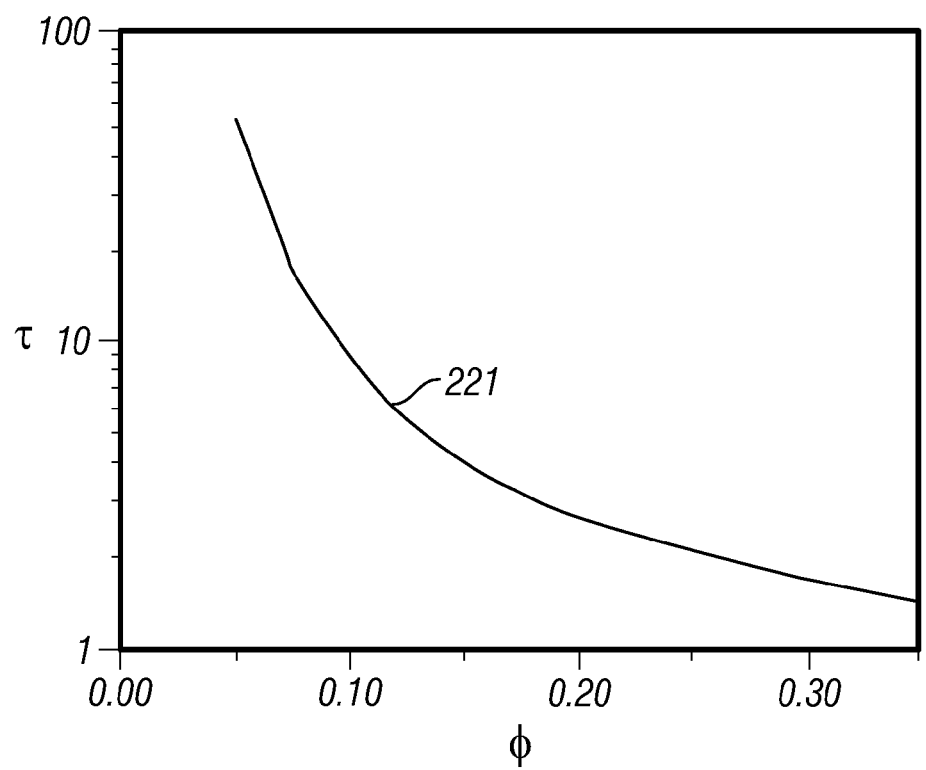
FIG. 5 (prior art) shows tortuosity as a function of porosity for the sandstone model of FIGS. 4a-4c.

Porosity for a particular sphere pack is readily determined from the Delaunay tessellation of the sphere pack. This tessellation is a method of dividing the packing into non-overlapping tetrahedral cells. The cells fit together to completely fill the packing volume. The porosity is simply the ratio of the total void volume of the cells to the total volume of the cells. The tortuosity is the product of the porosity and the formation factor. The formation factor can be calculated from a pore-space network extracted from the tessellation without the use of adjustable parameters. FIG. 5a is a plot of the tortuosity 221 as a function of porosity.

To complete the Gassmann calculations, the frame moduli are calculated from Digby's grain-contact theory that requires four microstructural parameters: a, Z, and R. The porosity is determined from the Delaunay cell tessellation described above. Using the known location of each sphere in the compacted/cemented packing, the number of contacts for each sphere and the radius of the area of each contact are readily calculated. The averages of these values over the packing give the values of a and Z. The sphere radius R is fixed by the desired degree of simulated cementation.

Figure 6A:
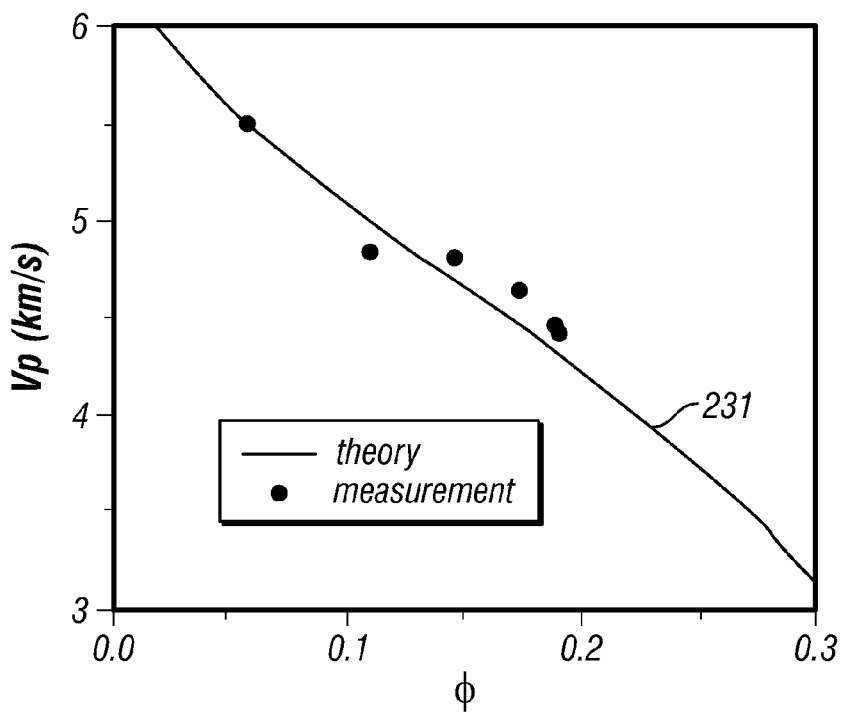
FIGS. 6a and 6b (prior art) show the modeled and actual dependence of compressional and shear wave velocities on porosity.
Figure 6B:
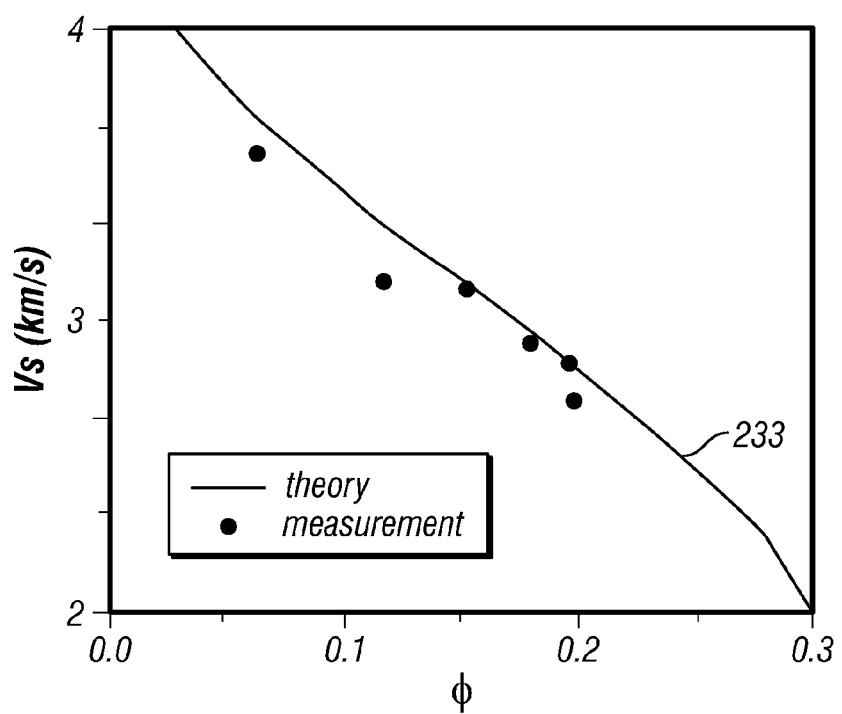

Bryant and Raikes also do calculations of elastic moduli using the Berryman effective medium theory. These are not discussed in detail here and the complete discussion is given in Bryant and Raikes. FIGS. 6a and 6b show plots of the compressional velocity $V_p$ as a function of porosity, and the shear velocity $V_s$ as a function of porosity respectively. The solid curves give the theoretical results for the pore-scale model while the individual points represent actual measurements on sandstones. Agreement is reasonably good. It should be noted that equivalent elastic parameters such as bulk modulus (or its reciprocal, compliance), shear modulus (or its reciprocal, compliance) and/or Poisson's ratio could also be modeled. These equivalent parameters are not easy to measure at normal logging speeds.

In one embodiment of the present invention, the porosity $\phi$ of the pore-geometrical model is adjusted heuristically to mimic known geological processes. This has been discussed in Bryant and Raikes. In addition to the compaction and quartz overgrowth discussed above, the present invention also envisages simulation of shale infilling. The porosity reduction of dispersed shale can be mimicked simply by randomly infilling the pore space. In all of the approaches, the porosity is decreased from the original porosity (~36%) until it agrees with measured porosity (e.g., wireline and/or MWD or LWD data, sidewall core data).

Given that there are many ways to reduce the porosity of the pore-geometric model one must choose one of the models. In one embodiment of the invention, a log-measured shale indicator, $V_{shale}$ (e.g., from a gamma ray log, SP log, or CBW from NMR measurements) is used. $V_{shale}$ may also be obtained from the difference in porosity derived from a neutron porosity measurement and the porosity derived from a density porosity measurement. If the $V_{shale}$ indicator exceeds some minimum value then dispersed shale is used to infill the pores until the model $\phi$ and the measured $\phi$ agree. This may be continued until available pore space is in-filled. If the apparent $V_{shale}$ is still less than the log indicated $V_{shale}$ then sand grains can be replaced with shale. The approach can be further refined by using a Thomas-Steiber approach to determine the shale distribution. A similar approach can be used to model autogenic shale.

Infilling the inter-granular porosity with shale mimics dispersed shale. It is generally accepted that the shale material contains ineffective porosity which does not contribute to fluid flow but increases the bound water. One can account for the shale porosity in a more complex approach which involves increasing both the pore-filling shale and the grain diameter. For example the volume of dispersed shale can be increased in proportion to the log-measured $V_{shale}$ and in particular it can be increased by randomly adding shale with a given $\phi_{shale}$ until the $\phi_{shale} \cdot V_{shale}$ equals the NMR-derived Clay Bound Water, CBW, and the pore geometric model porosity equals the log measured porosity:

The tessellation method discussed in Bryant and Raikes was originally discussed in Bryant and Blunt for the problem of fluid flow through porous media. Flow in such a porous medium is addressed by dividing the space into tetrahedra defined by the spheres, and defining an equivalent network model of the pore space. The network model now consists of pores or void spaces connected by narrower constrictions or throats. Each cell represents a pore and each cell face is a throat. The aggregation of cell pore volumes is used to calculate the porosity of the network and the fluid saturation when different cells are occupied by different fluids. The flow paths between adjacent cells are modeled by cylinders whose radii and length are hydrodynamically equivalent to the real pore space. The basic relations are:

$$Q = g\Delta P \quad (3),$$

where Q is the volume of fluid entering or leaving the medium in unit time, $\Delta P$ is the pressure drop and g is the hydrodynamic conductivity. For Poiseuille flow in a cylinder of radius r and length l, $$g = \frac{\pi r^4}{8\mu l}. \quad (4)$$

Figure 7:
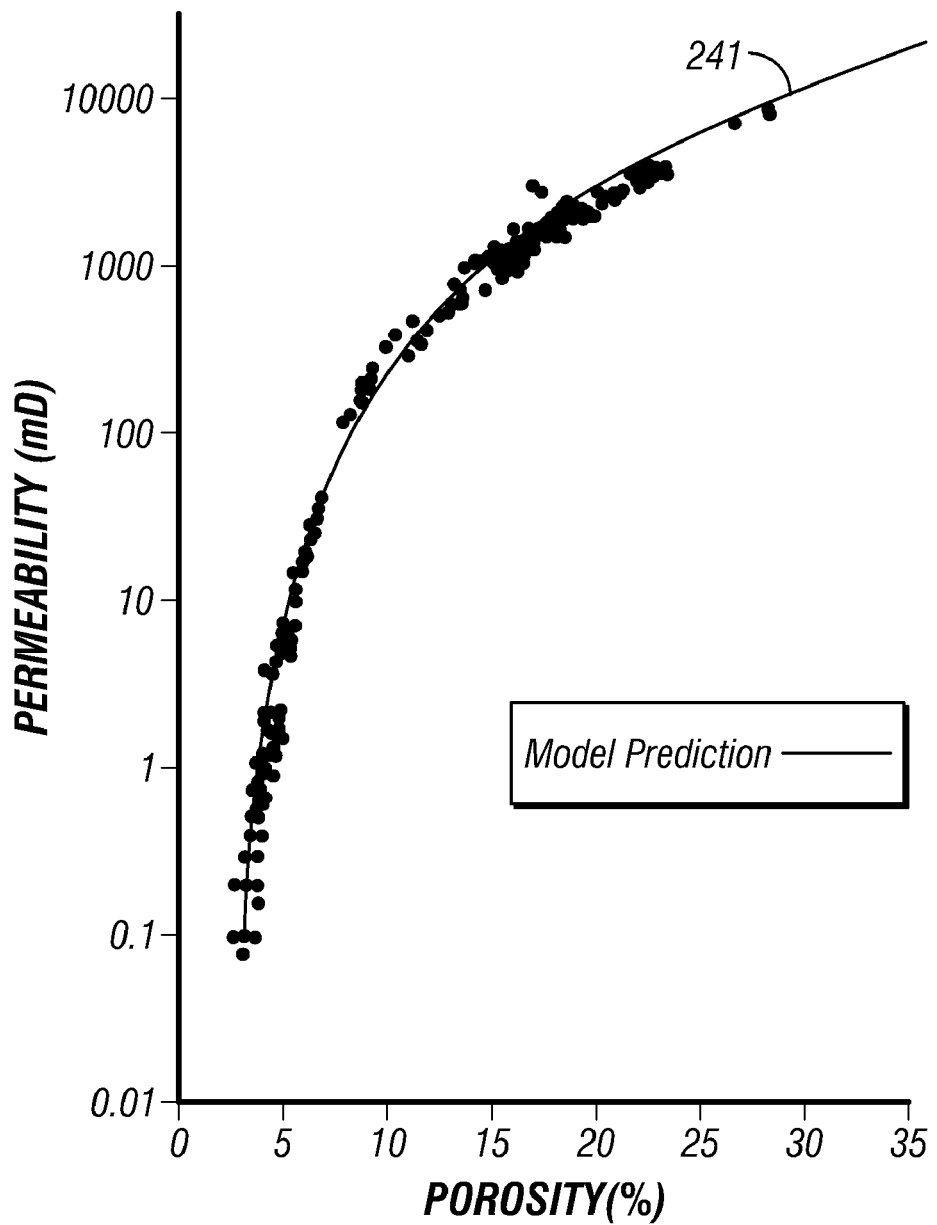
FIG. 7 (prior art) shows a comparison of the modeled and measured permeability as a function of porosity for a sandstone.

Bryant and Blunt show comparisons of their model prediction of permeability as a function of porosity both single phase flow and multiphase flow. FIG. 7 shows such a comparison for measurements made on the Fountainbleau sandstone with the solid line being the model prediction and the individual points are measurements on different samples of the Fountainbleau sandstone. Agreement is good.

For two phase flow, Bryant and Blunt defines a wetting phase and a non-wetting phase. They consider the effects of surface tension which results in a contact angle $\theta$ which defines the angle at which the fluid interface approaches a solid surface. Initially, the wetting phase is hydraulically connected throughout the rock along a network of sub-pore-scale roughness. Non-wetting fluid is allowed to access the network through a fraction of the faces or throats chosen at random on the outer boundary of the pack. The model assumes that the non-wetting fluid enters the pack sequentially through throats with successively smaller throat radius. Using this simple model, the mercury permeability injection was simulated. Bryant and Blunt showed a good comparison between predicted and actual values of relative permeability for a wide range of water saturation, different rates of flow for viscous flow and capillary flow. A detailed description of the physics of the model for multiphase flow is found in Blunt et al. (2002).

Another problem in which pore scale modeling has been used is that of prediction of NMR properties of earth formations. Toumelin et al. simulate the NMR response of porous rocks using a continuous, three-dimensional (3D) random-walk algorithm that solves Bloch-Torrey equations. The Bloch-Torrey equations, sometimes called the Bloch equations, describe the macroscopic nuclear magnetization of an assemblage of nuclear spins in a magnetic field. Toumelin solves the Bloch equations along the diffusion pathways of individual fluid molecules within a 3D porous synthetic grain packs designed to be geologically meaningful. The general method discussed by Toumelin provides a rigorous treatment of $T_1$ and $T_2$ relaxations with a minimum of assumptions and for arbitrary pulse sequences. Toumelin also discusses the issue of numerical accuracy of the simulation. The method explicitly accounts for diffusion in porous media, fluid wettabilities, and fluid spatial distributions. Toumelin concluded that currently available 2D NMR methods cannot correctly diagnose substantial diffusion coupling in carbonate rocks.

Figure 8:
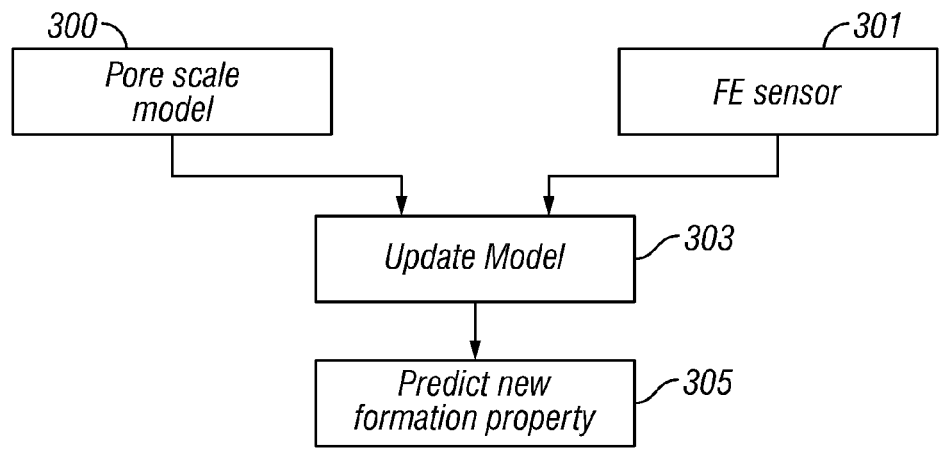
FIG. 8 is flow chart illustrating a method of the present invention using log measurements.

Turning now to FIG. 8, the basic concept underlying one embodiment of the invention is discussed. Measurements are made with a formation evaluation sensor 301 such as an acoustic sensor, a density sensor, a porosity sensor, or an NMR sensor. When acoustic sensors are used, both compressional and shear wave velocities may be measured. When an NMR sensor is used, as noted above, the pulse sequences should be chosen so that estimates of $T_1$, $T_2$ and D are obtained. In certain cases, it may be sufficient to get at least one of $T_1$, $T_2$ and D. The outputs of the FE sensor are matched with the outputs of a pore scale model 300 and, based on the comparison, the parameters of the pore scale model are altered 303.

In one embodiment of the invention, the FE sensor is a porosity sensor. The porosity may be determined directly from a neutron porosity device, NMR, or may be inferred from a gamma ray device in combination with knowledge of the lithology of the earth formation. The porosity of the pore-scale model is adjusted to match the observed porosity. Once this has been done, the formation permeability, formation factor and surface to volume (S/V) probability distribution function is calculated. This has been discussed above with reference to FIG. 7 and Bryant and Blunt.

In another embodiment of the invention the FE sensor is an NMR sensor. It is common practice to interpret the NMR data in terms of a pore size distribution. The pore size distribution can then be used in the pore scale model to determine other parameters that are harder to measure.

Nuclear magnetic resonance are particularly useful because of they contain information about grain size. Without such information it is difficult to make accurate predictions of some important properties of the rock, such as absolute permeability and capillary pressure curves. Numerical simulations are by their nature dimensionless, and therefore their results must be scaled appropriately to obtain desired dimensional properties. Measured spectrum of NMR relaxation times provides an opportunity to infer grain size for the successful scaling of dimensionless predictions.

NMR techniques have been employed in petroleum industry to either predict permeability or for fluid typing. The former application uses the surface relaxation mechanism to relate measured relaxation time spectra with surface-to-volume ratios of the pores and then use in permeability correlations. The usual approach is based on Brownstein and Tarr [8] model. They considered the diffusion equation for total magnetization with surface-like sinks and obtained exact solution for the magnetization decay in isolated spherical pore, which is the sum of decreasing exponential functions. Moreover, they have shown, that in the fast diffusion limit, given by $$\rho r/D \ll 1 \quad (5),$$

where $\rho$ is surface relaxivity, r is the radius of spherical pore, and D is water diffusivity. The lowest relaxation mode has much larger amplitude than other modes, and in this case the magnetization decays in time as a single exponential function:

$$M(t) = M_0 \exp(-t/T_2), \quad (6),$$

where $M_0$ is the initial magnetization and the transverse relaxation time $T_2$ is given by $$\frac{1}{T_2} = \rho \frac{S}{V}, \quad (7)$$

where S/V is the surface-to-volume ratio of the pore.

The model, described by eqns. (5-7) is applied now widely in petroleum industry, often disregarding assumptions that were used in its derivation. The real pore space, however, does not consist of isolated spherical pores, but is rather a complicated network-like structure of pore bodies connected by throats that restrict diffusion. Non-sphericity of pores questions the derivation of eqns. (5-7). Higher relaxation modes of the single pore may give significant contribution in the case of real pore space, since the assumptions under which they can be neglected may not be satisfied. Presence of connections between pores makes possible pore-to-pore coupling, when proton can diffuse sufficient distance to travel through several pores. The relaxation time of such a proton would correspond to surface-to-volume ratio of all the pores traveled. The limit of fast diffusion would not always be satisfied as well. For example, in the presence of pore-lining clay minerals, such as chlorite, which is often associated with high iron surface content and has very high surface-to-volume ratio, magnetic moment of proton will relax almost immediately at the moment when proton reaches pore wall. Evidently, such relaxation regime can not be considered to be in fast diffusion limit.

Figure 9:
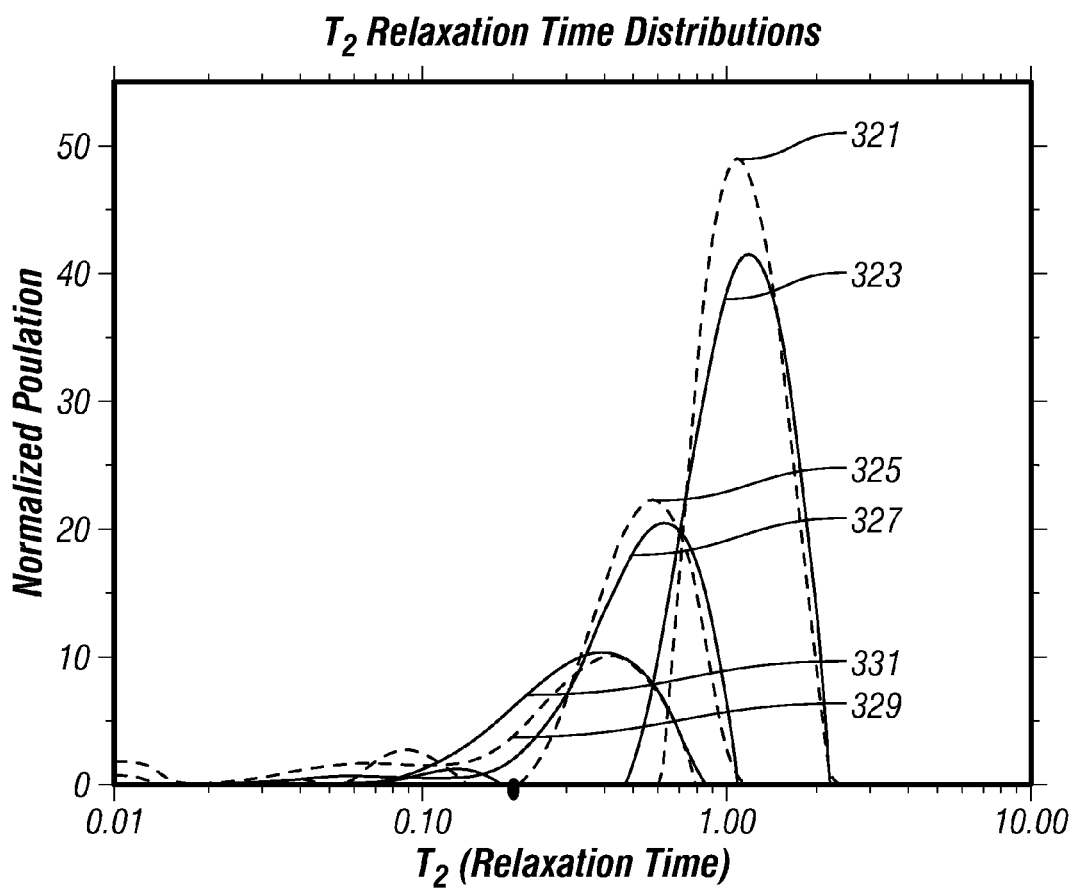
FIG. 9 (prior art) is a plot comparing experimental NMR $T_2$ distribution with simulation results for a packing of fused glass beads.
Figure 10:
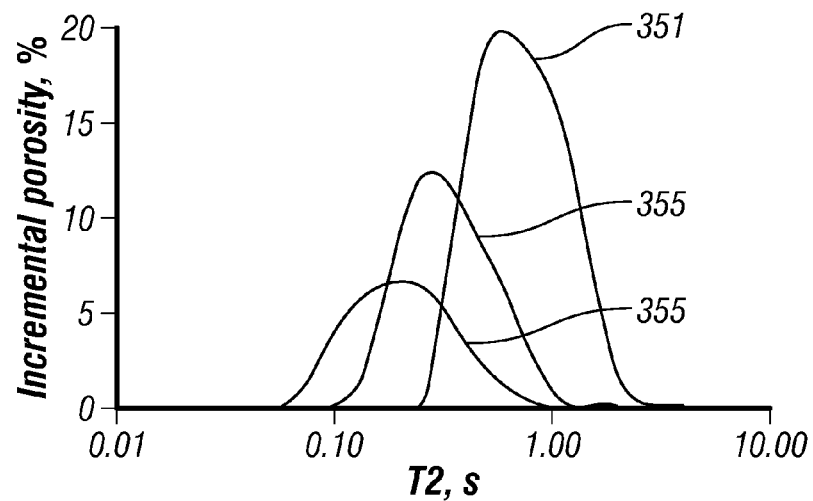
FIG. 10 (prior art) is a plot of predicted NMR $T_2$ distribution for numerical packing with cement overgrowth.

In one embodiment of the present invention, Delaunay tessellation subdivides pore space of the packing into tetrahedral pores. Surface-to-volume ratio is easily computed for each pore. If the values of grain size and surface relaxivity are specified, the application of eq. (7) immediately yields $T_2$ spectrum for the packing fully saturated with water. FIGS. 9 and 10 depict a comparison between experimental $T_2$ spectra and predicted $T_2$ spectra. FIG. 9 shows the comparison for experimental 321 and predicted 323 spectra for unconsolidated glass beads with a grain diameter of 100 μm for a porosity $\phi=0.38$. The curves 325, 327 show a similar comparison for $\phi=0.22$, while 329, 331 shows results for $\phi=0.14$. FIG. 10 shows the predicted distribution for the numerical packing with overgrowth cement at porosities of 0.36 (351), 0.22 (353) and 0.14 (355) respectively. The agreement between measured and simulated spectra is very good.

When pore space is partially saturated, it is still possible to predict $T_2$ distribution using eqn. (7). During either drainage (fluid is drained from the rock) or imbibition (fluid is added to a dry rock), the morphology of the wetting phase is computed, including fully saturated pores, menisci of the wetting phase and pendular rings. See SPE90333 and Gladkikh (Ph.D Dissertation, University of Texas at Austin, 2005). The distribution of fluids in the pore space will be different during drainage and imbibition, resulting in different properties.

Figure 11:
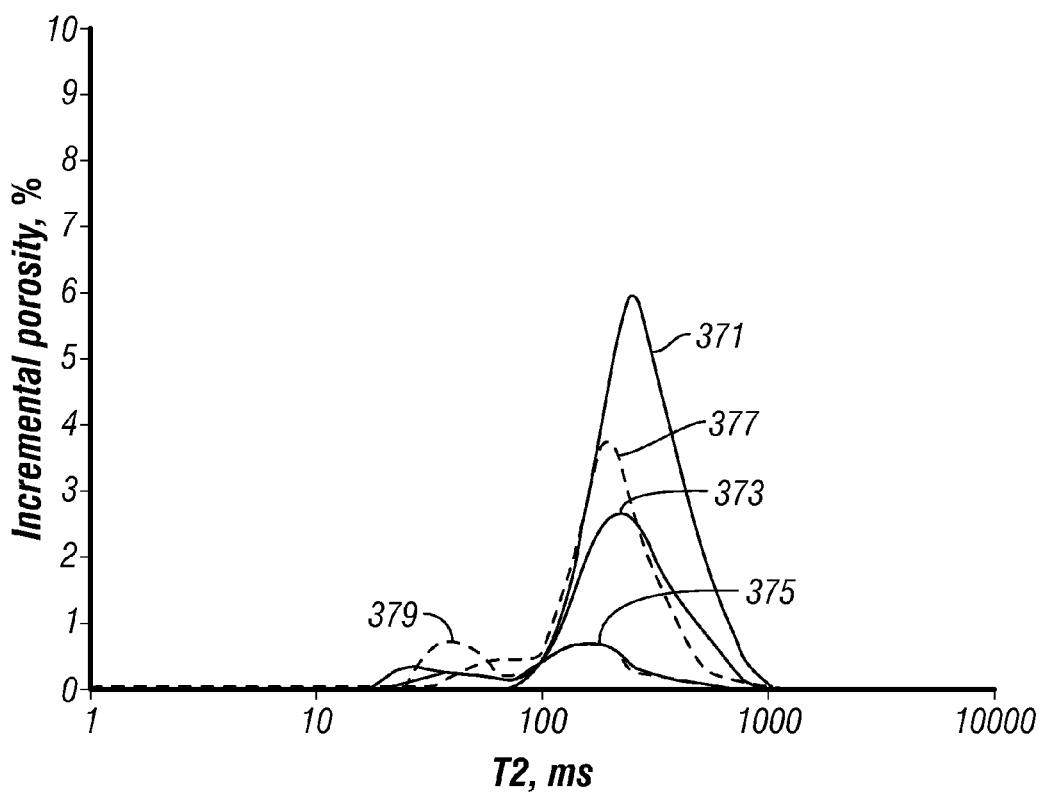
FIG. 11 is a plot of simulated NMR $T_2$ distribution for unconsolidated packing during drainage and imbibition.

Referring to FIG. 11, the curve 371 is for 100% wetting-phase saturation ($S_w$). The curve 373 is for $S_w=0.53$ during draining and 375 is for $S_w=0.18$ while draining. The curve 377 is for $S_w=0.19$ during imbibition and 379 is for $S_w=0.58$ during imbibition. The grain diameter was taken as 100 μm and the surface relaxivity was $2.6 \times 10^{-3}$ cm/s. The contact angle was taken as 0°.

Figure 12:
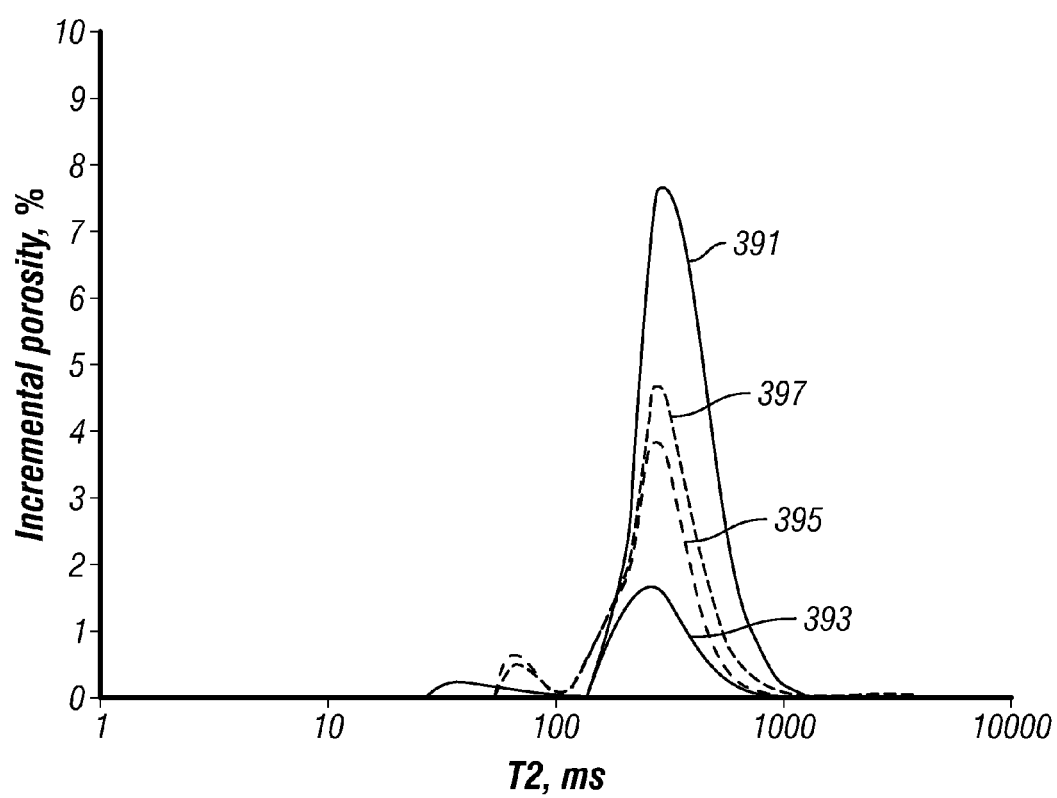
FIG. 12 is a plot of simulated NMR $T_2$ distribution for cemented packing during drainage and imbibition.

FIG. 12 shows results for a glass packing having $\phi=0.187$ with overgrowth cement. 391 is for $S_w=1$., 393 is for Sw=0.25 drained, 395 is for $S_w=0.49$ during imbibition and 397 is for $S_w=0.63$ during imbibition.

It can be seen on FIGS. 11 and 12 that as wetting-phase saturation decreases, the peak in the distribution that corresponds to fully saturated pores decreases (non-wetting phase occupies some of the pores), shifts to the left (wetting phase remains in small pores), and additional peak at much smaller times appears. This new peak corresponds to the contribution from pendular rings and menisci to the total signal. All of these effects are usually observed in laboratory experiments.

A commonly used prior art model is that of Coates et al, which estimates the permeability using subdivision of the relaxation spectrum into the contributions from "movable" (free fluid index—FFI) and "capillary bound" (bulk water irreducible—BVI) fluids:

$$K_C = C\phi^4 \left(\frac{FFI}{BVI}\right)^2. \quad (8)$$

Here C is an empirical constant and FFI+BVI=φ. For a given $T_2$ distribution the relative values of FFI and BVI are defined by some threshold value of transverse relaxation time $T_{2cutoff}$. This threshold is also purely empirical; the value of 33 ms is commonly used for sandstones. The basis of eqn. (8) is a Kozeny-Carman type relationship for permeability derived from the bundle of capillary tubes model. Therefore, eqn. (8) suffers from the internal inconsistency. The derivation is based, first, on eqns. (5-7) valid for the isolated spherical pore, and, second, on a Kozeny-Carman approach, valid for parallel non-intersecting capillary tubes. Moreover, in order to use eqn. (8) one must first determine two empirical constants ($T_{2cutoff}$ and C), which questions practical applicability of the model.

Figure 13:
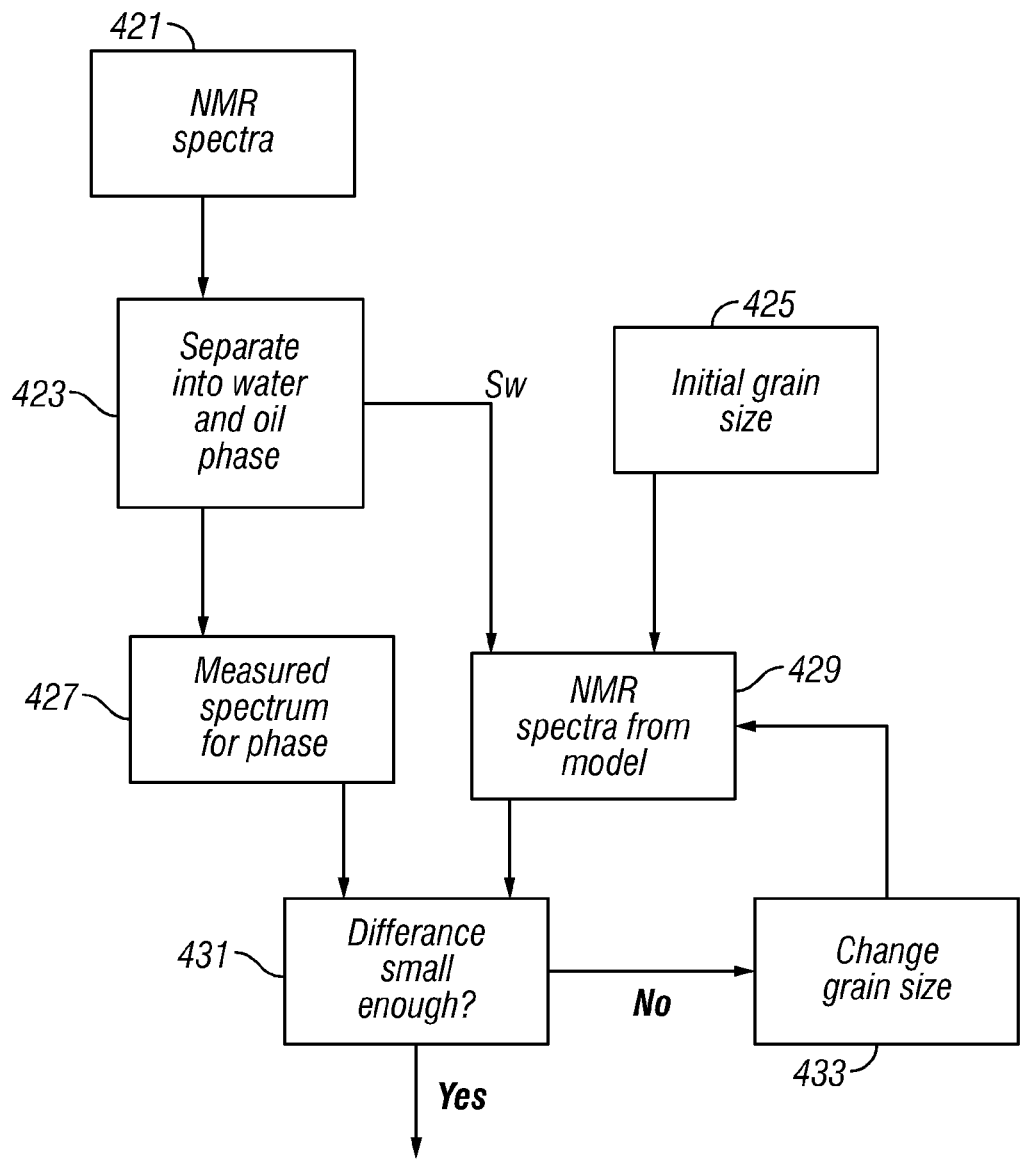
FIG. 13 is a flow chart of an embodiment of the invention used for determination of grain size of a model whose output matches an observed spectrum.

In the present invention, a different approach is used. The method is illustrated by the flow chart of FIG. 13. The method starts with the NMR relaxation spectra 421. The spectra may be longitudinal relaxation time ($T_1$) spectra or transverse relaxation time ($T_2$) spectra. We discuss an example in which $T_2$ spectra are used, but this is not to be construed as a limitation of the invention. The spectrum is subdivided into the contributions from the water and oil phase 423. This may be done, for example, using the diffusivity contrast between oil and water. This then gives a signal only from water 427. In parallel, a grain size for a pore-scale model is selected 425 and NMR spectra are predicted 429 for the particular wetting-phase saturation in the real data. This includes the effect of drainage or imbibition depending upon the reservoir conditions. The measured spectrum is compared with the model 431 simulated output. If the difference between the spectra is too large, the grain size is changed 433 and the pore-scale model output recomputed 429. To infer mean value of grain size we simulate relaxation time distribution for a range of grain sizes numerically. We choose that grain size, which provides the closest fit to the measured data. As a criterion for the fitting we use the minimization of quadratic error:

$$R_{grain} = \min_{R_{grain}^j} \left( \sum_{i=1}^{N_{bins}} (\phi_i^{sim} - \phi_i^{meas})^2 \right). \quad (9)$$

This value of grain size is used to scale computed dimensionless permeability to its dimensional value. It should be noted here that such a methodology allows inverting $T_2$ relaxation spectrum to compute absolute permeability of the formation. However, it is entirely based on Brownstein-Tarr model (Eqs. (5-7)). It should be noted that the simulation proceeds in a similar manner for both $T_1$ and $T_2$ relaxation time distributions.

Figure 14:
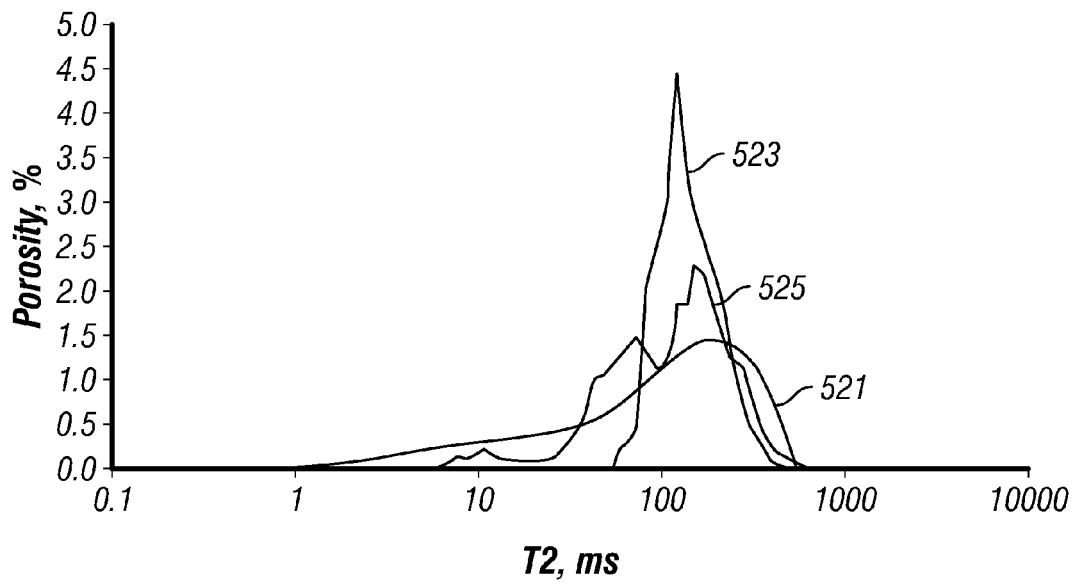
FIG. 14 is a comparison between measured and simulated $T_2$ distribution.

To predict permeability of the samples we used NMR relaxation time distribution and eqn. (9) to infer grain size. Two types of simulations were made. In the first simulation, we assume that the rock consists of quartz grains with overgrowths and the value of surface relaxivity is the same for all depths. This value ($2.3 \times 10^{-3}$ cm/s) is estimated by matching both $T_2$ distribution and measured air permeability for the sample with the highest value of permeability. FIG. 14 shows the actual NMR $T_2$ distribution 521 along with the best fit 523 obtained by selecting a grain size based on eqn. (9).

The second type of simulation uses more complicated pore-scale model and attempts to utilize mineralogical information. From X-ray diffraction data for two samples we know that there is about 2-3% kaolinite and 5% chlorite (both are weight percentages) present in the sample. Therefore, we introduced into the pore space 2% (weight) of pore-filling clay with the following parameters: clay porosity is 50%; surface relaxivity is $2.0 \times 10^{-2}$ cm/s; density is 2.8 g/cm$^3$. It was assumed that hydraulic conductivity of this clay is negligible. To take into account pore-lining clay, we assumed that the surface of each grain within each tetrahedral pore can have altered value of surface relaxivity with probability 5%. This altered value represents the much faster surface relaxivity of chlorite and was chosen to be $2.0 \times 10^{-2}$ cm/s. The remaining rock material was supposed to be quartz with overgrowths, having the value of surface relaxivity $2.6 \times 10^{-3}$ cm/s. All the parameters are essentially unknown a priori and are assumed so that predicted $T_2$ distribution provides good agreement with the measured distribution. These parameters, however, are not empirical, as for example, is the $T_{2cutoff}$ value used in Coates model given by eqn. (8). They have physical nature and can, in principle, be measured independently. The result is shown by 525 in FIG. 14. When no data are available (for example, in log interpretation in the absence of core data) surface relaxivity of quartz, reported in the literature may be used. See, for example SPE22723 of Coates et al.

Figure 15:
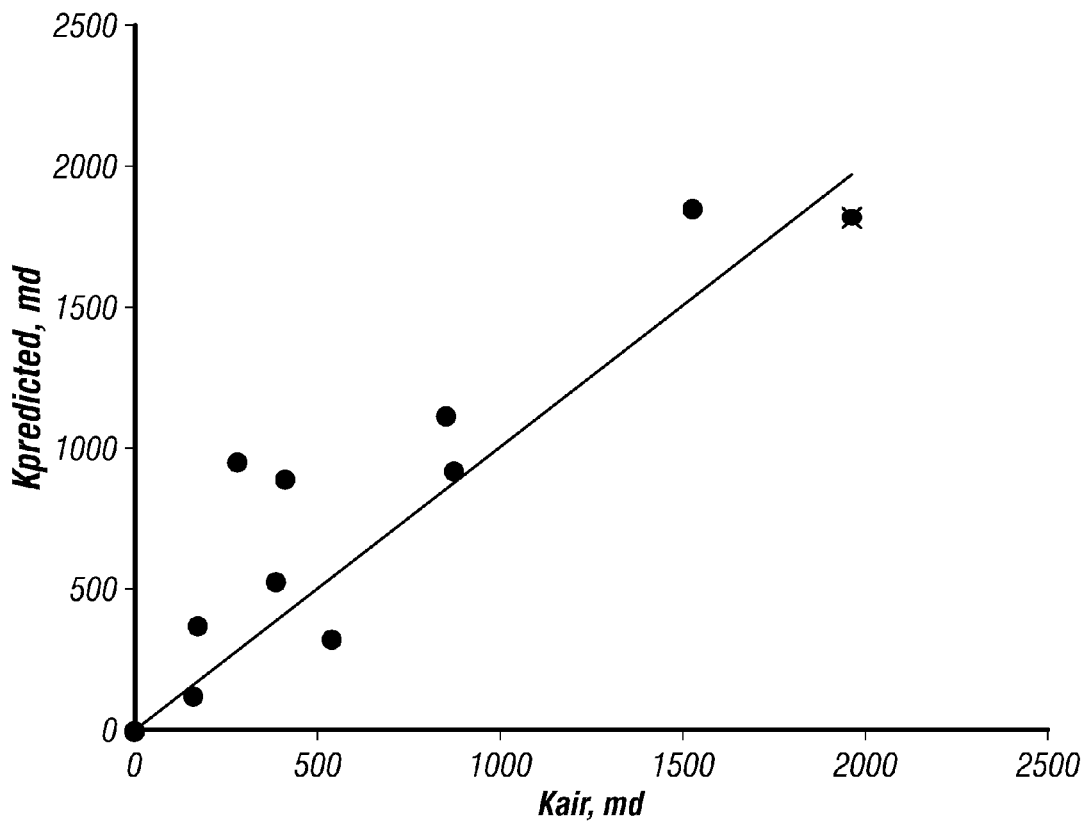
FIG. 15 is a comparison between measured permeability and the predicted permeability for cores from the Hawkins field.

Turning now to FIG. 15, a comparison of measured air permeability (abscissa) against the predicted air permeability using the first simulation method discussed above, i.e., with no clay infilling (ordinate) is shown. The comparison is reasonably good. Additional simulation was done using the second method, i.e, with clay infilling, was done, but in this case only a marginal improvement was obtained.

Figure 16:
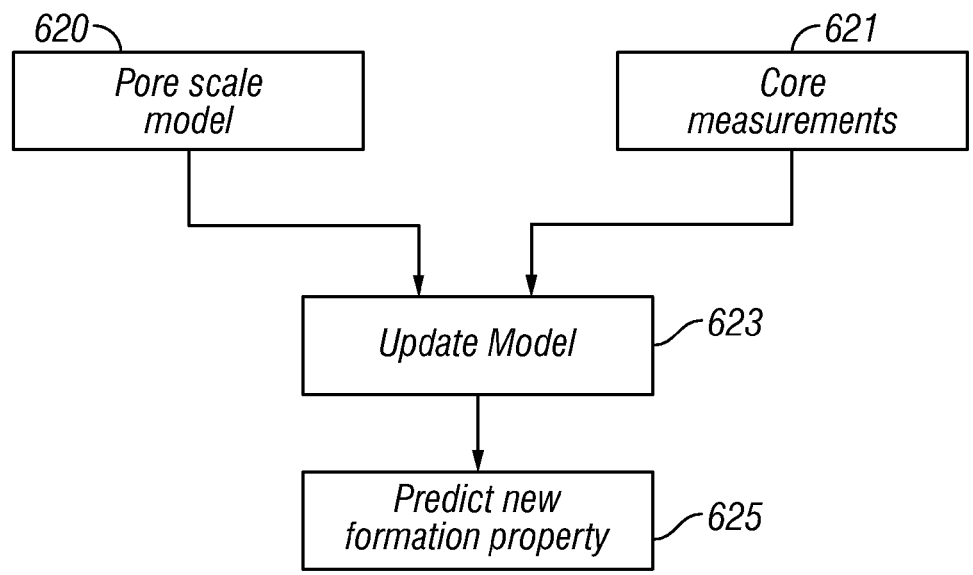
FIG. 16 is a flow chart illustrating a method of the present invention using core measurements.

In another embodiment of the invention shown in FIG. 16, instead of using measurements from a first FE sensor to adjust 623 the pore-scale model 620, core measurements 621 are used. Cores may be obtained from core barrels conveyed at the end of a drillstring or may be sidewall cores obtained using percussion or rotary drilling. Such coring devices are well known in the art. For the purposes of this invention, the coring devices should be such as to maintain the integrity of the core samples so that conventional and/or special analysis of the cores can be made at the surface.

The surface analysis typically involves preparing a thin section of the core sample for examination under a microscope. Based on the examination of the thin sections, porosity and a grain size distribution can be estimated. In addition, the amount of quartz overgrowth can also be determined from a thin section. It is preferable but not essential that the porosity estimate made in surface measurements be corrected for downhole stress conditions. As noted in Domenico (1977), the total change in porosity for a sand pack studied ranged from 0.3817 at 400 psi (2.76 MPa) to 0.3672 at 5000 psi (34.5 MPa). For consolidated sandstones where quartz overgrowth has cemented the sand grains together, the porosity change is even less due to the high elastic modulus of quartz. The thin section observations may include the amount of dispersed shale in the core, the determined values being part of the pore-space model and may be used for permeability calculations.

Using the parameters determined from the thin sections, it is possible to predict 625 in situ properties such as permeability using the method of Bryant et al. (1993)

without making flow measurements on either the core sample, or flow measurements in the well. One problem of interest is in laminated reservoirs where there is vertical heterogeneity. By obtaining core samples from the different layers and estimating permeability in the different layers, estimates may be made of the bulk permeability in horizontal and vertical directions. As is well known, the horizontal permeability in a laminated reservoir is a weighted average of the permeabilities in the individual layers. The permeability in a direction perpendicular to bedding is obtained by a weighted average of the reciprocals of the permeability.

Figure 17:
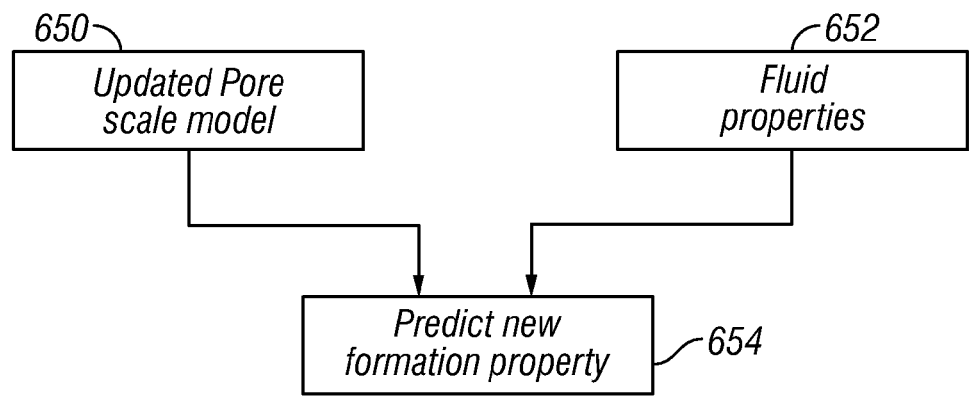
FIG. 17 is a flow chart illustrating a method of the present invention in which a pore scale model is used to derive additional formation properties using values of properties of a fluid in the pore space.

Another embodiment of the invention (FIG. 17) starts with an updated pore scale model of rock properties 650 and uses obtained fluid properties 652 to determine properties of a reservoir 654. The fluid properties may be obtained, for example, from NMR measurements (in situ or on recovered formation fluids), and/or from measurements made on recovered formation fluids. Formation fluids can be recovered, for example, using the method and apparatus described in U.S. Pat. No. 5,303,775 of Michaels et al., U.S. Pat. No. 6,557,632 to Cernosek, or U.S. Pat. No. 6,157,893 to Berger et al. The first three are example of wireline devices while the last one is an example of a MWD device. Specific examples of determination of reservoir properties are discussed next.

Figure 18:
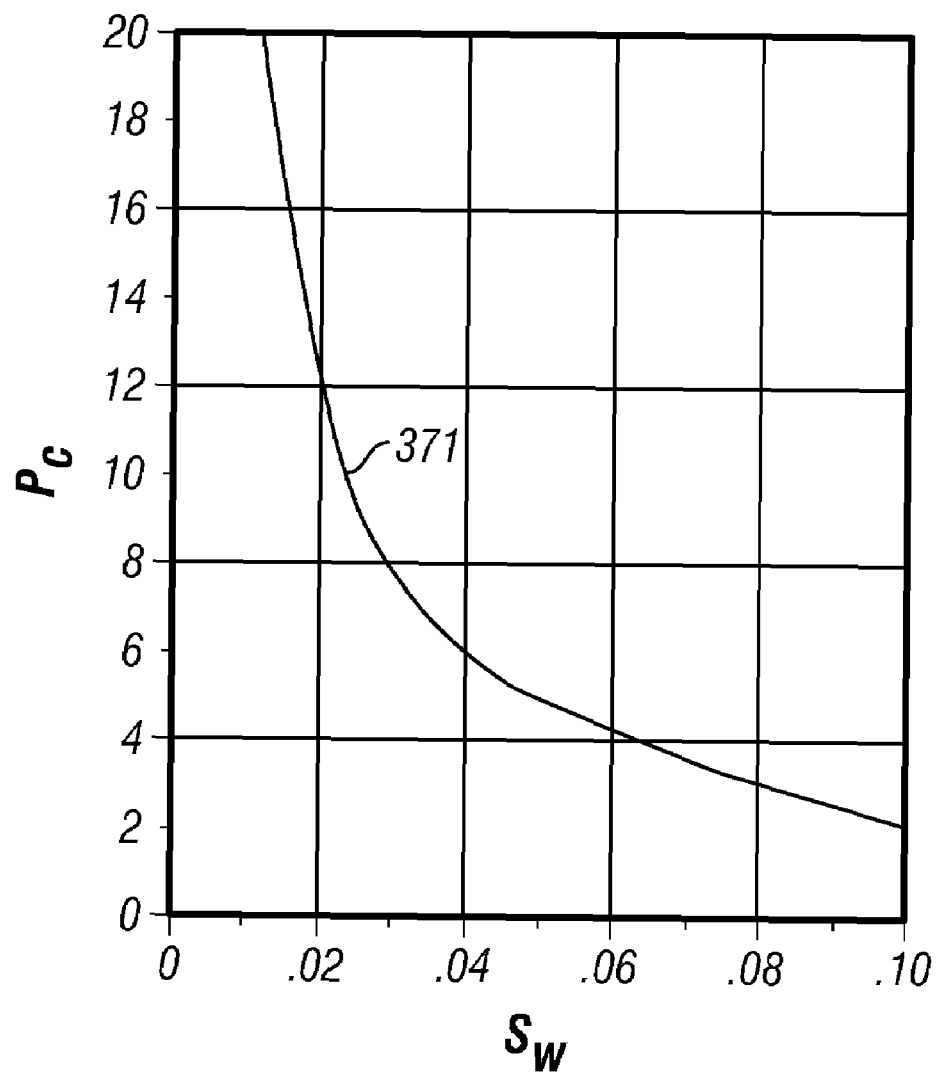
FIG. 18 is an exemplary plot of capillary pressure as a function of fluid saturation derived from a pore scale model and assumed values of interfacial surface tension.

In one embodiment of the invention, a relation between capillary pressure and water saturation may be determined. As noted in Hirasaki (3-1), the capillary pressure $P_c$ across an interface is given by $$P_c = \frac{2\sigma}{r} \tag{10}$$

where $\sigma$ is the interfacial surface tension. The pore scale model discussed above gives a pore size distribution model from which a fluid saturation such as water saturation $S_w$ may be determined. Eqn. (10) also gives a direct relation between the pore size and the capillary pressure. Thus, it is possible to derive a relation between capillary pressure and fluid saturation from the pore scale model and knowledge of the interfacial surface tension. Using an assumed value of $\sigma$ (or value of $\sigma$ determined by other means) and the previously determined pore size distribution, the capillary pressure distribution can be obtained, and thus the water saturation that gives the capillary pressure is obtained. The relation is depicted by 371 in FIG. 18.

From knowledge of the capillary pressure curve (obtained above using the cumulative distribution of pore radii), the water saturation as a function of elevation above the free water level can be calculated. As noted in Hirasaki (3-3), this requires satisfying the condition:

$$P_c(S_w) = (\rho_w - \rho_o)gh \tag{11},$$

where the $\rho$'s are densities (subscript w refers to water and subscript o refers to oil or hydrocarbon), g is the acceleration due to gravity and h is the height of the water column having a saturation $S_w$.

Figure 19:
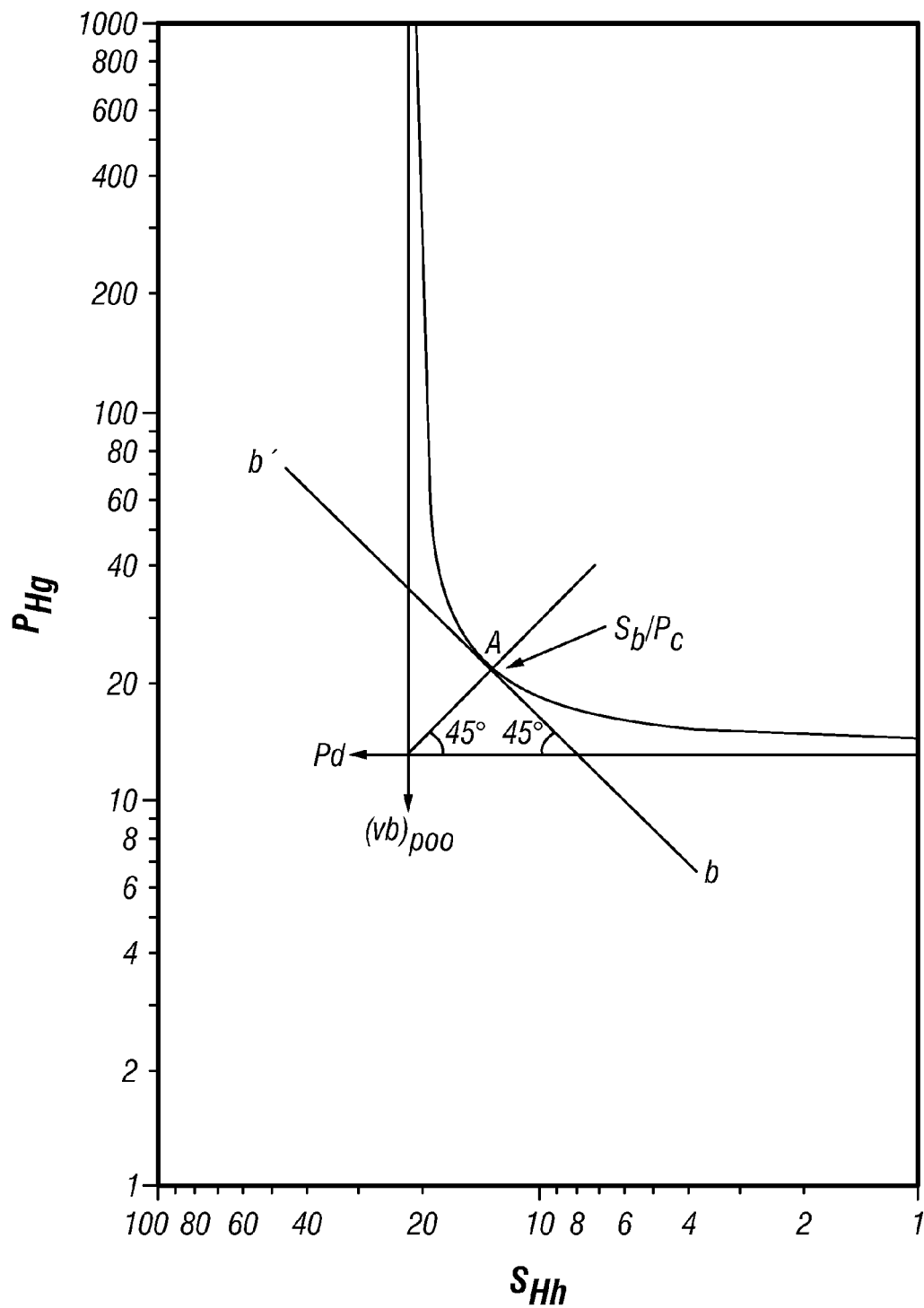
FIG. 19 is a plot useful in determining brine permeability from a capillary pressure-saturation curve.

In another embodiment of the invention, brine permeability may be estimated for a particular pore scale model. One method uses a methodology developed by Swanson. The $P_c$-S relation is developed for mercury using the method outlined above. As disclosed by Swanson, this relation is plotted on a log-log scale. On the log-log plot, the particular ratio of $S_b/P_c$ at which the plot is asymptotic to a 45° line is determined (see FIG. 19). The brine permeability is then given by a relationship of the form:

$$K_w = C\left(\frac{S_b}{P_c}\right)^B, \tag{12}$$

where B and C are calibration constants and $K_w$ is the brine permeability. It should be noted that the particular form of eqn. (12) is not to be construed as a limitation to the method: what is important is that the brine permeability can be determined from a mercury saturation curve that is derivable from the pore scale geometric model.

The present invention also envisages determination of relative permeabilities of a mixture of fluids. An exemplary method is given by Purcell using the Pc-S curves as:

$$k_{rw} = \frac{\int_0^{S_w} dS_w/(P_c)^2}{\int_0^1 dS_w/(P_c)^2} \tag{13}$$

where $k_{rw}$ and $S_w$ are the relative permeability and saturation of the wetting phase. Similarly, the relative permeability of the non-wetting phase is given by:

$$k_{ro} = \frac{\int_{S_w}^1 dS_w/(P_c)^2}{\int_0^1 dS_w/(P_c)^2}. \tag{14}$$

It should be noted that the method given by Purcell is only for exemplary purposes, and other relations such as those from Burdine or Corey may be used. The Burdine model introduces a tortuousity factor $\lambda_{rw}$ of the wetting phase:

$$k_{rw} = (\lambda_{rw})^2 \frac{\int_0^{S_w} dS_w/(P_c)^2}{\int_0^1 dS_w/(P_c)^2}, \tag{15}$$

where $$\lambda_{rw} = \frac{\tau_w(1.0)}{\tau_w(Sw)} = \frac{S_w - S_m}{1 - S_m} \tag{16}$$

where Sm is the minimum wetting phase saturation from the capillary pressure curve, $\tau_w(1.0)$ and $\tau_w(S_w)$ are the tortuousities of the wetting phase when the wetting phase saturation is equal to 100% and Sw respectively. Other models such as the Corey model and/or the Corey-Brooks model may also be used.

Figure 20:
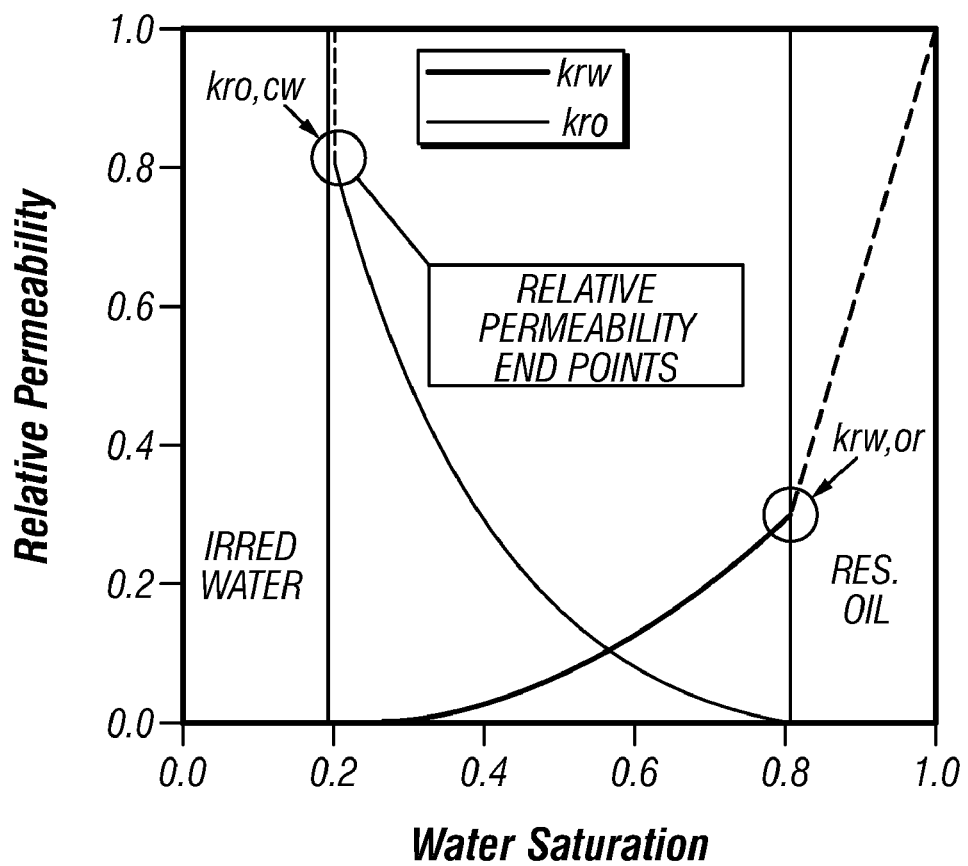
FIG. 20 shows plots of relative permeabilities for a two phase mixture of fluids in the pore space of a rock formation.

End point mobility may also be determined using an assumed value of viscosity (or a measured value such as from NMR measurements). As seen in FIG. 20, there are two end-point relative permeabilities. The first is the relative permeability of hydrocarbons (i.e., oil or gas) at irreducible water saturation $k_{ro,swirr}$ and is of interest when drilling in water-wet zones using an oil-based mud. The other is the relative permeability of water at residual oil saturation $k_{rw,or}$. The latter quantity is of interest in secondary recovery operations and when drilling in hydrocarbon zones using a water-based mud. Corresponding to these endpoints, we have mobilities defined by:

$$M_1 = \frac{k_{rw,or}}{\mu_w} \quad (11)$$

$$M_2 = \frac{k_{ro,swirr}}{\mu_o},$$

and the end-point mobility ratio $M=M_1/M_2$. The quantity $k_{rw,or}$ is of particular interest in water flooding projects where the oil saturation is at residual saturation.

In one embodiment of the invention, directional measurements are made. These directional measurements can be made using directional FE sensors. Alternatively, directional core analysis is done, either from oriented sidewall cores or by azimuthal sampling of bottom-hole cores. This makes it possible to develop pore-scale geometric models that are azimuthally dependent, and thus predict azimuthally dependent properties of the reservoir. Measurements made by orientation sensors discussed above are used in this determination of azimuthal properties.

In another embodiment of the invention the pore-scale models of electric current flow (Bryant and Pallatt, 1996; Gladkikh, 2005) is used to predict formation factor. This may be done directly from the pore scale model, and does not require knowledge of grain size. Knowledge of water saturation allows then predicting resistivity index; and knowledge of water electrical conductivity—predicting formation resistivity. As described in Bryant and Pallatt, 1996, current I flows from a site j to a neighboring site k according to $$I=g_{jk}(V_j-V_k) \quad (13).$$

The conductivity of the packing is given by a relation of the form:

$$\sigma_0 = \frac{4\pi I^{SS}}{\frac{dV}{d(1/r)}}, \quad (14)$$

where $I^{SS}$ is the steady state current through the network induced by a spherical potential gradiant, V is the average voltage at network sites within a thin spherical shell of radius r, and $\sigma_0$ is the conductivity of the porous medium filled with conducting fluid. Customarily, the conductivity is expressed in terms of the formation factor $$F = \frac{\sigma_w}{\sigma_0}, \quad (15)$$

where $\sigma_w$ is the conductivity of the formation fluid.

When a conducting phase such as brine is mixed with a non-conducting phase such as oil or gas, current only flows through a sub-network of the pore-space network. The sub-network is defined by the continuous conducting phase in the network. The conductivity $\sigma_t$ of this sub-network relative to the conductivity of the pore-space network when it contains only a conducting phase $\sigma_0$ is given by the resistivity index $$I_R = \frac{\sigma_t}{\sigma_0}. \quad (14)$$

The invention has been described above with reference to a device that is conveyed on a wireline into the borehole. The method of the invention may also be used with a logging device conveyed into a borehole on a tubular, such as a drillstring. The logging device may also be conveyed downhole on a slickline, the data stored in a suitable memory device and processed subsequent to retrieval of the slickline. The processing of the data may be done downhole using a downhole processor at a suitable location. It is also possible to store at least a part of the data downhole in a suitable memory device, in a compressed form if necessary. Upon subsequent retrieval of the memory device during tripping of the drillstring, the data may then be retrieved from the memory device and processed uphole.

Implicit in the control and processing of the data is the use of a computer program on a suitable machine readable medium that enables the processor to perform the control and processing. The machine readable medium may include ROMs, EPROMs, EEPROMs, Flash Memories and Optical disks.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of evaluating an earth formation, the method comprising:
    (a) obtaining Nuclear Magnetic Resonance (NMR) signals from the earth formation;
    (b) defining a model of the earth formation, the model including grains;
    (c) simulating a NMR response using the defined model;
    (d) adjusting a grain size of the model using the simulated response and the NMR signals;
    (e) using the adjusted model to estimate a value of an additional property of the formation; and
    (f) producing a log of the additional property of the formation.

2. The method of claim 1 wherein simulating the NMR response further comprises simulating an NMR relaxation time spectrum and wherein adjusting the parameter further comprises:
    (i) deriving a magnetization relaxation spectrum from the NMR signals;
    (ii) adjusting the grain size using a difference between the NMR relaxation time spectrum and the magnetization relaxation spectrum.

3. The method of claim 2 wherein the derived relaxation spectrum is selected from the group consisting of (i) a longitudinal relaxation time ($T_1$) spectrum, and (ii) a transverse relaxation time ($T_2$) spectrum.

4. The method of claim 2 wherein deriving the magnetization relaxation spectrum uses a wetting phase selected from (i) water, and (ii) oil.

5. The method of claim 2 wherein simulating the NMR relaxation time spectrum further comprises using a saturation of a wetting phase.

6. The method of claim 2 wherein simulating the NMR relaxation time spectrum further comprises using one of (i)

drainage of a wetting fluid in pore-spaces of the model, and (ii) imbibition of a wetting fluid in pore-spaces of the model.

7. The method of claim 1 wherein adjusting the grain size of the model further comprises using a least-squares minimization.

8. The method of claim 1 wherein the additional property is selected from the group consisting of (i) a permeability, (ii) a formation factor, and, (iii) an S/V probability distribution function.

9. The method of claim 1 wherein simulating the NMR response further comprises at least one of (i) adding a material to a pore space of the model, (ii) accounting for quartz overgrowth, (iii) accounting for pore-filling dispersed shale, and (iv) accounting for compaction.

10. An apparatus for evaluating an earth formation, the apparatus comprising:
   (a) a nuclear magnetic resonance (NMR) sensor configured to be conveyed in a borehole in the earth formation; and
   (b) a processor configured to:
      (A) define a model of the earth formation, the model including grains;
      (B) simulate an NMR response using the defined model;
      (C) adjust a grain size of the model using the simulated NMR response and NMR signals obtained by the NMR sensor;
      (D) use the adjusted model to estimate an additional property of the formation; and
      (E) produce a log of the additional property of the formation.

11. The apparatus of claim 10 wherein the processor is further configured to:
   (i) simulate the NMR response by simulating an NMR relaxation time spectrum;
   (ii) derive a magnetization relaxation spectrum from the NMR signals; and
   (iii) adjust the parameter using a difference between the NMR relaxation time spectrum and the magnetization spectrum.

12. The apparatus of claim 11 wherein the derived relaxation spectrum is selected from the group consisting of (i) a longitudinal relaxation time ($T_1$) spectrum, and (ii) a transverse relaxation time ($T_2$) spectrum.

13. The apparatus of claim 11 wherein the processor is further configured to derive the magnetization relaxation spectrum using a wetting phase selected from (i) water, and (ii) oil.

14. The apparatus of claim 11 wherein the processor is configured to simulate the NMR relaxation time spectrum by further using a saturation of a wetting phase selected from (i) water, and (ii) oil.

15. The apparatus of claim 11 wherein the processor is configured to simulate the NMR relaxation time spectrum by further using one of (i) drainage of a wetting fluid in pore-spaces of the model, and (ii) imbibition of a wetting fluid in pore-spaces of the model.

16. The apparatus of claim 10 wherein the processor is configured to adjust the parameter of the model by further using a least-squares minimization.

17. The apparatus of claim 10 wherein the additional property is selected from the group consisting of (i) a permeability, (ii) a formation factor, and, (iii) an S/V probability distribution function.

18. The apparatus of claim 10 wherein the processor is configured to simulate the NMR response by at least one of (i) adding a material to a pore space of the model, (ii) accounting for quartz overgrowth, (iii) accounting for pore-filling dispersed shale, and (iv) accounting for compaction.

19. The apparatus of claim 10 further comprising a conveyance device configured to convey the NMR sensor into the borehole, the conveyance device selected from (i) a wireline, and (ii) a drilling tubular.

20. A computer-readable medium for use with an apparatus for evaluating an earth formation, the apparatus comprising:
   (a) a nuclear magnetic resonance (NMR) sensor conveyed in a borehole in the earth formation;
   the medium comprising instructions that enable a processor to:
   (b) define a model of the earth formation, the model including grains;
   (c) simulate an NMR response using the defined model;
   (d) adjust a grain size of the model using the simulated NMR response and signals obtained by the NMR sensor;
   (e) estimate a value of an additional property of the earth formation; and
   (f) ft produce a log of the estimated additional property.

21. The medium of claim 20 further comprising at least one of:
   (i) a ROM, (ii) an EPROM, (iii) an EPROM, (iv) a Flash Memory, and (v) an optical disk.

22. The method of claim 1 wherein the earth formation comprises clastics and the grains comprise grains of clastics.

23. The apparatus of claim 10 wherein the earth formation comprises clastics and the grains comprise grains of clastics.

* * * * *

UNITED STATES PATENT AND TRADEMARK OFFICE
CERTIFICATE OF CORRECTION

PATENT NO.       : 7,363,161 B2                                              Page 1 of 1
APPLICATION NO.  : 11/445023
DATED            : April 22, 2008
INVENTOR(S)      : Daniel T. Georgi, Mikhail Gladkikh and Songhua Chen It is certified that error appears in the above-identified patent and that said Letters Patent is hereby corrected as shown below:

Column 22, line 41 claim 20, delete the word "ft";

Column 22, line 44 claim 21, change "(iii) an EPROM," to read --(iii) an EEPROM,--;

Signed and Sealed this

Eighth Day of July, 2008

JON W. DUDAS
*Director of the United States Patent and Trademark Office*